US012746075B2

(12) United States Patent
Timperley et al.

(10) Patent No.: US 12,746,075 B2
(45) Date of Patent: Sep. 29, 2026

(54) SYSTEM AND METHOD FOR ROBOTICALLY ASSISTING A SURGICAL PROCEDURE

(71) Applicant: MAKO Surgical Corp., Weston, FL (US)

(72) Inventors: John Timperley, Exeter (GB); Ross Crawford, Brisbane (AU); Jonathan Howell, Cullompton (GB); Matthew Hubble, Woodbury (GB); Matthew Wilson, Salterton (GB); Matthew Thompson, Woodbridge, CT (US); Graham Gie, Exton (GB)

(73) Assignee: MAKO Surgical Corp., Weston, FL (US)

( * ) Notice: Subject to any disclaimer, the term of this patent is extended or adjusted under 35 U.S.C. 154(b) by 141 days.

(21) Appl. No.: 18/413,105

(22) Filed: Jan. 16, 2024

(65) Prior Publication Data

US 2024/0148452 A1 May 9, 2024

Related U.S. Application Data

(63) Continuation of application No. 17/894,207, filed on Aug. 24, 2022, now Pat. No. 11,903,662, which is a (Continued)

(51) Int. Cl.
*A61F 2/46* (2006.01)
*A61B 34/00* (2016.01)
(Continued)

(52) U.S. Cl.
CPC .............. *A61B 34/30* (2016.02); *A61B 34/20* (2016.02); *A61B 34/70* (2016.02); *A61F 2/4607* (2013.01);
(Continued)

(58) Field of Classification Search
CPC ........ A61F 2/46; A61F 2/4603; A61F 2/4607; A61F 2002/4631; A61F 2002/4632;
(Continued)

(56) References Cited

U.S. PATENT DOCUMENTS 5,456,686 A 10/1995 Klapper et al.
5,769,092 A * 6/1998 Williamson, Jr. . G05B 19/4099 128/923
(Continued)

FOREIGN PATENT DOCUMENTS

WO 0110356 A2 2/2001
WO WO-03077101 A2 * 9/2003 ............. A61B 90/06
(Continued)

OTHER PUBLICATIONS

Stryker SA, "Exeter X3 RimFit Acetabular Cup Surgical Protocol Brochure", 2010, 20 pages.
(Continued)

*Primary Examiner* — Eric S Gibson
(74) *Attorney, Agent, or Firm* — Howard & Howard Attorneys PLLC

(57) ABSTRACT

Surgical systems and methods for robotically-assisted insertion of a stem implant into a cavity of a bone. A manipulator includes a robotic arm that supports an end effector which detachably receives the stem implant. A navigation system includes a localizer to track poses of the bone and the end effector. Controller(s) coupled to the manipulator and the navigation system obtain a surgical plan defining a planned relationship between the stem implant and the bone. Based on the tracked poses and the surgical plan, the controller(s) control the manipulator to enable movement of the end effector and the stem implant to facilitate insertion of the stem implant into the cavity.

14 Claims, 15 Drawing Sheets

Related U.S. Application Data continuation of application No. 17/024,035, filed on Sep. 17, 2020, now Pat. No. 11,471,226, which is a continuation of application No. 16/039,805, filed on Jul. 19, 2018, now Pat. No. 10,806,529.

(60) Provisional application No. 62/534,991, filed on Jul. 20, 2017.

(51) Int. Cl.
*A61B 34/20* (2016.01)
*A61B 34/30* (2016.01)
*A61B 34/10* (2016.01)

(52) U.S. Cl.
CPC . *A61B 2034/107* (2016.02); *A61B 2034/2055* (2016.02); *A61B 2034/2057* (2016.02); *A61B 2034/2059* (2016.02)

(58) Field of Classification Search
CPC . A61F 2002/4633; A61B 34/10; A61B 34/20; A61B 34/25; A61B 34/30; A61B 34/70; A61B 2034/107; A61B 2034/2055; A61B 2034/2057; A61B 2034/2059
See application file for complete search history.

(56) References Cited

U.S. PATENT DOCUMENTS

| | | | | |
|---|---|---|---|---|
| 5,806,518 | A * | 9/1998 | Mittelstadt | A61F 2/30942 600/407 |
| 5,993,458 | A | 11/1999 | Vaitekunas et al. | |
| 6,205,411 | B1 * | 3/2001 | DiGioia, III | A61F 2/46 703/11 |
| 6,395,007 | B1 | 5/2002 | Bhatnagar et al. | |
| 6,652,587 | B2 | 11/2003 | Felt et al. | |
| 6,884,264 | B2 | 4/2005 | Spiegelberg et al. | |
| 7,104,996 | B2 | 9/2006 | Bonutti | |
| 7,815,644 | B2 | 10/2010 | Masini | |
| 7,831,292 | B2 * | 11/2010 | Quaid | A61B 34/37 345/157 |
| 7,931,690 | B1 | 4/2011 | Bonutti | |
| 8,657,482 | B2 | 2/2014 | Malackowski et al. | |
| 8,709,016 | B2 | 4/2014 | Park et al. | |
| 8,852,210 | B2 * | 10/2014 | Selover | A61B 90/11 606/279 |
| 8,911,234 | B2 | 12/2014 | Mayer et al. | |
| 8,992,542 | B2 * | 3/2015 | Hagag | A61F 2/36 606/130 |
| 9,008,757 | B2 * | 4/2015 | Wu | A61B 34/20 600/407 |
| 9,119,655 | B2 * | 9/2015 | Bowling | A61B 34/10 |
| 9,220,612 | B2 | 12/2015 | Behzadi | |
| 9,289,301 | B2 | 3/2016 | Mayer et al. | |
| 9,381,085 | B2 | 7/2016 | Axelson, Jr. et al. | |
| 9,566,120 | B2 | 2/2017 | Malackowski et al. | |
| 9,566,121 | B2 | 2/2017 | Staunton et al. | |
| 9,888,939 | B2 | 2/2018 | Dorawa et al. | |
| 9,999,458 | B2 | 6/2018 | Mayer et al. | |
| 10,492,875 | B2 | 12/2019 | Janik et al. | |
| 10,806,529 | B2 * | 10/2020 | Timperley | A61B 17/8808 |
| 11,471,226 | B2 * | 10/2022 | Timperley | A61B 34/30 |
| 11,903,662 | B2 * | 2/2024 | Timperley | A61B 34/30 |
| 2004/0230199 | A1 | 11/2004 | Jansen et al. | |
| 2008/0058945 | A1 | 3/2008 | Hajaj et al. | |
| 2009/0043344 | A1 | 2/2009 | Schlotterback | |
| 2010/0061181 | A1 | 3/2010 | Malackowski et al. | |
| 2014/0039681 | A1 * | 2/2014 | Bowling | A61B 34/30 700/261 |
| 2014/0135791 | A1 * | 5/2014 | Nikou | A61F 2/4609 606/130 |
| 2014/0171962 | A1 | 6/2014 | Kang | |
| 2014/0188134 | A1 * | 7/2014 | Nortman | A61F 2/36 606/130 |
| 2014/0200621 | A1 | 7/2014 | Malackowski et al. | |
| 2014/0277549 | A1 | 9/2014 | Ell | |
| 2014/0303631 | A1 * | 10/2014 | Thornberry | A61F 2/4609 606/91 |
| 2016/0030126 | A1 | 2/2016 | Netravali et al. | |
| 2016/0374770 | A1 | 12/2016 | Janik et al. | |
| 2017/0000562 | A1 * | 1/2017 | Frank | A61B 17/80 |
| 2017/0189203 | A1 * | 7/2017 | Hagag | A61F 2/34 |
| 2017/0196711 | A1 * | 7/2017 | Behzadi | A61B 17/320068 |
| 2018/0092757 | A1 * | 4/2018 | Behzadi | A61F 2/389 |
| 2018/0228614 | A1 | 8/2018 | Lang et al. | |
| 2018/0368899 | A1 | 12/2018 | Sahin et al. | |
| 2019/0021796 | A1 * | 1/2019 | Timperley | A61B 17/8808 |
| 2019/0133790 | A1 | 5/2019 | Viscardi et al. | |
| 2019/0336306 | A1 * | 11/2019 | Ishikawa | A61F 2/3601 |
| 2019/0357986 | A1 | 11/2019 | Morgan et al. | |
| 2020/0008893 | A1 | 1/2020 | Janik et al. | |
| 2021/0000556 | A1 * | 1/2021 | Timperley | A61B 34/70 |
| 2022/0401164 | A1 * | 12/2022 | Timperley | A61B 34/70 |
| 2024/0148452 | A1 * | 5/2024 | Timperley | A61B 34/20 |

FOREIGN PATENT DOCUMENTS

| | | | | |
|---|---|---|---|---|
| WO | WO-2014074676 A2 * | 5/2014 | | A61B 34/30 |
| WO | WO-2017200785 A1 * | 11/2017 | | A61B 17/86 |

OTHER PUBLICATIONS

Stryker SA, "Primary V40 Surgical Protocol—Exeter Total Hip System", 2006, 20 pages.

* cited by examiner

SYSTEM AND METHOD FOR ROBOTICALLY ASSISTING A SURGICAL PROCEDURE

RELATED APPLICATIONS

The subject application is a continuation of U.S. patent application Ser. No. 17/894,207, filed Aug. 24, 2022, which is a continuation of U.S. patent application Ser. No. 17/024,035, filed Sep. 17, 2020, now U.S. Pat. No. 11,471,226, which is a continuation of U.S. patent application Ser. No. 16/039,805, filed Jul. 19, 2018, now U.S. Pat. No. 10,806,529, which claims the benefit of and priority to U.S. Provisional Patent App. No. 62/534,991, filed on Jul. 20, 2017, the contents and disclosure of each of the above applications being hereby incorporated by reference in their entirety.

TECHNICAL FIELD

The present disclosure relates generally to robotic systems, and more specifically, to a system and method for robotically assisting a surgical procedure.

BACKGROUND

Surgical procedures require the use of specialized tools to perform tasks requiring a high degree of accuracy and precision. Such surgical procedures require precise positioning of tools and/or implants relative to a patient's anatomy. Within the field of orthopedic procedures, the removal of tissue to create cavities, for example, within a bone, and the subsequent injection of an adhesive cement and placement of the implant rely on great care by the surgeon to successfully accomplish the procedure. This can be particularly challenging without the use of specialized guides, and is even more challenging in minimally invasive procedures where visibility at the surgical site is limited or nonexistent.

Prior solutions for enhancing precision and accuracy in aligning tools and/or implants involved the use of mechanical guides, fixtures, or jigs. These mechanical aids were placed or mounted in close proximity to the patient's target anatomy and provided physical boundaries beyond which the surgeon was prevented from going. Depending on the particular configuration, the mechanical aids were limited in their effective assistance with positioning and orienting tools and implants.

Although the available mechanical aids improved a surgeon's precision and accuracy, they required their own physical placement and alignment with the patient's anatomy that would likewise be subject to an operator's imprecision. The size of the physical aid may be larger than could be accommodated within the relatively small spaces allowed for minimally invasive surgery. Moreover, a considerable amount of time may be required to place and/or adjust the physical aids, which may prolong the surgical procedure and thus the duration a patient may be under anesthetic.

The present disclosure provides advantages and benefits over the conventional use of mechanical aids for guiding a surgeon during tissue removal, adhesive application, and implant placement and overcomes one or more of the problems set forth above and/or other problems in the art.

SUMMARY

According to one aspect, the present disclosure is directed to a robotic system. The robotic system may include a localizer, a surgical robotic manipulator; an end effector coupled to the manipulator; and a controller. The controller may be configured to receive signals from the localizer. The controller may also be configured to determine a final position of a cavity creation tool used to penetrate a portion of a patient's anatomy, where the determination is based on the signals received from the localizer. The controller may be configured to determine an implant insertion path for an implant to be inserted into a final implant position within the portion of the patient's anatomy, wherein the final implant position corresponds to the final position of the cavity creation tool. The controller may be configured to move the end effector with the implant coupled thereto such that the implant moves along the implant insertion path. The controller may be configured to terminate the movement of the end effector when the implant reaches the final implant position.

In the robotic system, the localizer may be configured to track a position of the portion of the patient's anatomy. The controller may further be configured to determine a movement of the portion of the patient's anatomy based on the signals received from the localizer. The controller may be configured to adjust the implant insertion path based on the determined movement of the portion of the patient's anatomy. The controller may be configured to cause the end effector to hold the implant in the final implant position until the controller determines that cement located adjacent to the implant has cured. The controller may be further configured to determine that the portion of the patient's anatomy moves based on signals received from the localizer, and to cause the end effector to move in synchrony with the portion of the patient's anatomy until the controller determines that the cement has cured.

The robotic system may further include a cement mixing apparatus that is configured to mix a predetermined amount of cement. The robotic system may further include a cement injector configured to inject the predetermined amount of cement into a cavity formed in the portion of the patient's anatomy corresponding to the final implant position. The controller may be further configured to control the cement mixing apparatus to mix the predetermined amount of cement for a first predetermined amount of time; and to control the cement injector to inject the predetermined amount of cement into the cavity at a predetermined pressure after the first predetermined amount of time has elapsed. The controller may be further configured to wait a second predetermined amount of time after the cement has been injected into the cavity; and to cause the implant to be inserted into the final implant position after the second predetermined amount of time has elapsed. The controller may be further configured to cause the end effector to hold the implant in the final implant position until a third predetermined time has elapsed. The controller may be further configured to cause the end effector to release the implant after the third predetermined amount of time has elapsed. The controller may be further configured to determine the implant insertion path such that the cement surrounds the implant when the implant is inserted into the final implant position.

In the robotic system, the cavity creation tool may be a broach. The broach may be configured to be removably coupled to the end effector. The broach may be coupled to a hand tool separate from the surgical robotic manipulator.

In another aspect, the present disclosure provides a robotic system including a localizer; a surgical robotic manipulator capable of detachably receiving an energy applicator and an implant; and a controller configured to receive signals from the localizer. The controller may be configured to determine a location within a portion of a patient's anatomy in which to form a cavity based on the signals received from the localizer. The controller may be configured to cause the energy applicator to form the cavity; and cause the surgical robotic manipulator to insert the implant into the cavity. The localizer may be configured to track a position of the portion of the patient's anatomy.

The robotic system may further include wherein the controller is configured to determine a movement of the portion of the patient's anatomy based on the signals received from the localizer. The controller may be configured to synchronize movement of the energy applicator with the determined movement of the portion of the patient's anatomy while the cavity is being formed. The controller may be configured to cause the manipulator to hold the implant in the cavity until the controller determines that cement adjacent to the implant has cured. The controller may be further configured to determine that the portion of the patient's anatomy moves based on signals received from the localizer; and to cause the implant to move in synchrony with the portion of the patient's anatomy until the controller determines that the cement has cured. The controller may cause the energy applicator to form the cavity with a predefined central axis in relation to the portion of the patient's anatomy. The robotic system may further include an end effector removably coupled to the manipulator, wherein the controller causes the end effector to insert the implant along the predefined central axis.

The robotic system may further include a cement mixing apparatus that is configured to mix a predetermined amount of cement. The robotic system further includes a cement injector configured to inject the predetermined amount of cement into the cavity. The robotic system may include wherein the controller is further configured to control the cement mixing apparatus to mix the predetermined amount of cement for a first predetermined amount of time; and to control the cement injector to inject the predetermined amount of cement into the cavity at a predetermined pressure after the first predetermined amount of time has elapsed. The controller may be further configured to wait a second predetermined amount of time after the cement has been injected into the cavity; and to insert the implant into the cavity after the second predetermined amount of time has elapsed. The robotic system may further comprise an end effector removably coupled to the manipulator, wherein the controller is further configured to cause the end effector to hold the implant in the cavity until a third predetermined time has elapsed. The controller may be further configured to cause the end effector to release the implant after the third predetermined amount of time has elapsed. The controller may be further configured to cause the energy applicator to form the cavity with a predetermined size and shape such that the cement surrounds the implant when the implant is inserted into the cavity.

The robotic system may further include wherein the controller is configured to cause the energy applicator to form a predetermined number of cement holes extending from a wall of the cavity into the portion of the patient's anatomy. The controller may be further configured to cause the energy applicator to form the predetermined number of cement holes with a predetermined depth, each cement hole being formed with a predetermined angle with respect to the central axis.

In yet another aspect, the present disclosure provides a method of robotically assisting a surgical implant procedure. The method includes providing a surgical robotic manipulator having an end effector removably attached thereto. The method includes receiving, by a controller, signals from a localizer. The method includes determining, by the controller, a final position of a cavity creation tool used to penetrate a portion of a patient's anatomy based on the signals received from the localizer. The method includes determining, by the controller, an implant insertion path for an implant to be inserted into a final implant position within the portion of the patient's anatomy, wherein the final implant position corresponds to the final position of the cavity creation tool. The method includes moving the end effector with the implant coupled thereto such that the implant moves along the implant insertion path. The method includes terminating the movement of the end effector when the implant reaches the final implant position.

The method may further include tracking a position of the portion of the patient's anatomy by the localizer. The method may include determining a movement of the portion of the patient's anatomy based on the signals received from the localizer. The method may further include adjusting the implant insertion path based on the determined movement of the portion of the patient's anatomy. The method may further include causing the end effector to hold the implant in the final implant position until the controller determines that cement located adjacent to the implant has cured. The method may further include determining that the portion of the patient's anatomy moves based on signals received from the localizer; and causing the end effector to move in synchrony with the portion of the patient's anatomy until the controller determines that the cement has cured.

The method may further include mixing a predetermined amount of cement using a cement mixing apparatus of the surgical robotic manipulator. The method may further include injecting the predetermined amount of cement into a cavity formed in the portion of the patient's anatomy corresponding to the final implant position using a cement injector of the surgical robotic manipulator. The method may further include controlling the cement mixing apparatus to mix the predetermined amount of cement for a first predetermined amount of time; and controlling the cement injector to inject the predetermined amount of cement into the cavity at a predetermined pressure after the first predetermined amount of time has elapsed. The method may further include waiting a second predetermined amount of time after the cement has been injected into the cavity; and causing the implant to be inserted into the final implant position after the second predetermined amount of time has elapsed. The method may further include causing the end effector to hold the implant in the final implant position until a third predetermined time has elapsed. The method may further include causing the end effector to release the implant after the third predetermined amount of time has elapsed. The method may further include causing the controller to determine the implant insertion path such that the cement surrounds the implant when the implant is inserted into the final implant position.

In yet another further aspect, the present disclosure provides method of robotically assisting a surgical implant procedure. The method includes providing a surgical robotic manipulator capable of detachably receiving an energy applicator and an implant. The method includes receiving, by a controller, signals from a localizer. The method includes determining, by the controller, a location within a portion of a patient's anatomy in which to form a cavity based on the signals received from the localizer so that the cavity can be formed at the location using the energy applicator. The method includes causing the surgical robotic manipulator to insert the implant into the cavity.

The method may further include tracking a position of the portion of the patient's anatomy by the localizer. The method may further include determining a movement of the portion of the patient's anatomy based on the signals received from the localizer. The method may further include synchronizing movement of the energy applicator with the determined movement of the portion of the patient's anatomy while the cavity is being formed. The method may further include causing the manipulator to hold the implant in the cavity until the controller determines that cement adjacent to the implant has cured. The method may further include determining that the portion of the patient's anatomy moves based on signals received from the localizer; and causing the implant to move in synchrony with the portion of the patient's anatomy until the controller determines that the cement has cured. The method may further include controlling, by the controller, the energy applicator to form the cavity with a predefined central axis in relation to the portion of the patient's anatomy. The method may further include controlling, by the controller, an end effector of the surgical robotic manipulator to insert the implant along the predefined central axis.

The method may further include mixing a predetermined amount of cement using a cement mixing apparatus of the surgical robotic manipulator. The method may further include injecting the predetermined amount of cement into the cavity using a cement injector of the surgical robotic manipulator. The method may further include controlling the cement mixing apparatus to mix the predetermined amount of cement for a first predetermined amount of time; and controlling the cement injector to inject the predetermined amount of cement into the cavity at a predetermined pressure after the first predetermined amount of time has elapsed. The method may further include waiting a second predetermined amount of time after the cement has been injected into the cavity; and causing the surgical robotic manipulator to insert the implant into the cavity after the second predetermined amount of time has elapsed. The method may further include causing the surgical robotic manipulator to hold the implant in the cavity until a third predetermined time has elapsed. The method may further include causing the surgical robotic manipulator to release the implant after the third predetermined amount of time has elapsed. The method may further include controlling, by the controller, the energy applicator to form the cavity with a predetermined size and shape such that the cement surrounds the implant when the implant is inserted into the cavity. The method may further include controlling, by the controller, the energy applicator to form a predetermined number of cement holes extending from a wall of the cavity into the portion of the patient's anatomy. The method may further include controlling, by the controller, the energy applicator to form the predetermined number of cement holes with a predetermined depth, each cement hole being formed with a predetermined angle with respect to the central axis.

BRIEF DESCRIPTION OF THE DRAWINGS

Advantages of the present disclosure will be readily appreciated, as the same becomes better understood by reference to the following detailed description, when considered in connection with the accompanying drawings. Non-limiting and non-exhaustive embodiments of the present disclosure are described with reference to the following figures, wherein like numerals refer to like parts throughout the various views unless otherwise specified.

DETAILED DESCRIPTION

In the following description, numerous specific details are set forth in order to provide a thorough understanding of the present invention. It will be apparent, however, to one having ordinary skill in the art that the specific details need not be employed and/or not be employed exactly as described to practice the present invention. In some instances, well-known materials or methods have not been described in detail in order to avoid obscuring the present invention.

Figure 1:
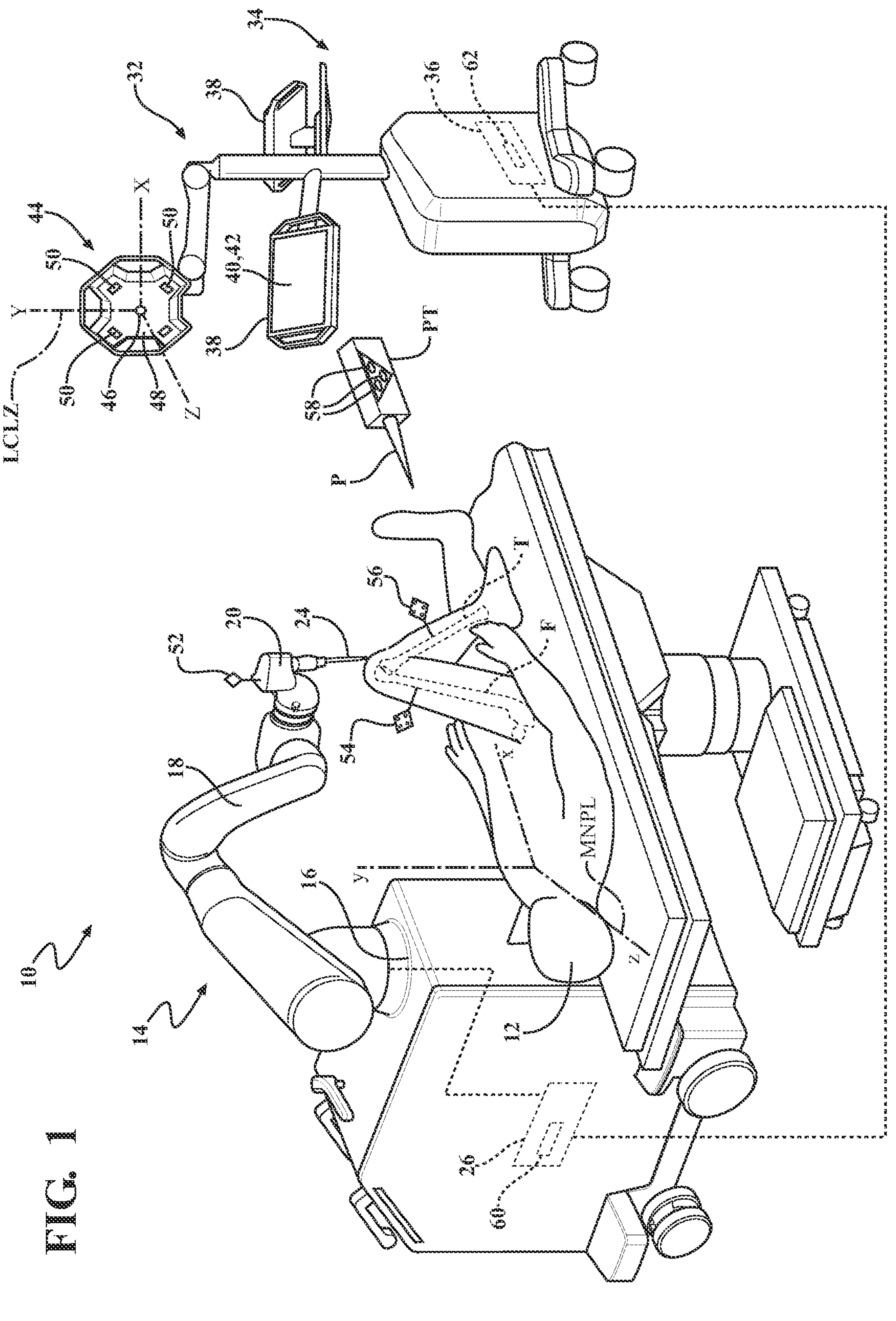
FIG. 1 is a perspective view of a system for manipulating an anatomy of a patient.

FIG. 1 is a perspective view of a system 10 for manipulating an anatomy of a patient 12. More specifically, system 10 is a robotic surgical cutting system for cutting away material from the anatomy of the patient 12, such as bone or soft tissue. In FIG. 1, the patient 12 is undergoing a surgical procedure. The anatomy in FIG. 1 includes a femur (F) and a tibia (T) of the patient 12. The anatomy also includes an acetabulum (not shown in FIG. 1). The surgical procedure may involve tissue removal and may also involve the insertion of one or more implants or grafts (e.g., bone or cartilage grafts, real or artificial ligaments, etc.) into a portion of the patient's anatomy. In some embodiments, the surgical procedure involves partial or total knee or hip replacement surgery. Some of the types of implants that may be used in the surgical procedure are shown in U.S. Pat. No. 9,381,085, entitled, "Prosthetic Implant and Method of Implantation," the disclosure of which is hereby incorporated by reference. Those skilled in the art appreciate that the system and method disclosed herein may be used to perform other procedures, surgical or non-surgical, or may be used in industrial applications or other applications where robotic systems are utilized.

The system 10 includes a surgical robotic manipulator 14. The manipulator 14 has a base 16 and a linkage 18. The linkage 18 may comprise links forming a serial arm or parallel arm configuration. An end effector 20 removably couples to the manipulator 14 and is movable relative to the base 16 to interact with the surgical environment, and more specifically, the anatomy. The end effector 20 is grasped by the operator. One exemplary arrangement of the manipulator 14 and the end effector 20 is described in U.S. Pat. No. 9,119,655, entitled, "Surgical Manipulator Capable of Controlling a Surgical Instrument in Multiple Modes," the disclosure of which is hereby incorporated by reference. The manipulator 14 and the end effector 20 may be arranged in alternative configurations. The end effector 20 includes an energy applicator 24 designed to contact the tissue of the patient 12 at the surgical site. The end effector 20 may have various configurations depending on the application. The energy applicator 24 may be a cavity creation tool, such as a drill, a saw blade, a bur, an ultrasonic vibrating tip, a probe, a stylus, a reamer, a rasp, impactor, or the like. The manipulator 14 also houses a manipulator computer 26, or other type of control unit. The end effector 20 can be like that shown in U.S. Pat. No. 9,566,121, entitled, "End Effector of a Surgical Robotic Manipulator," which is hereby incorporated by reference.

Figure 2:
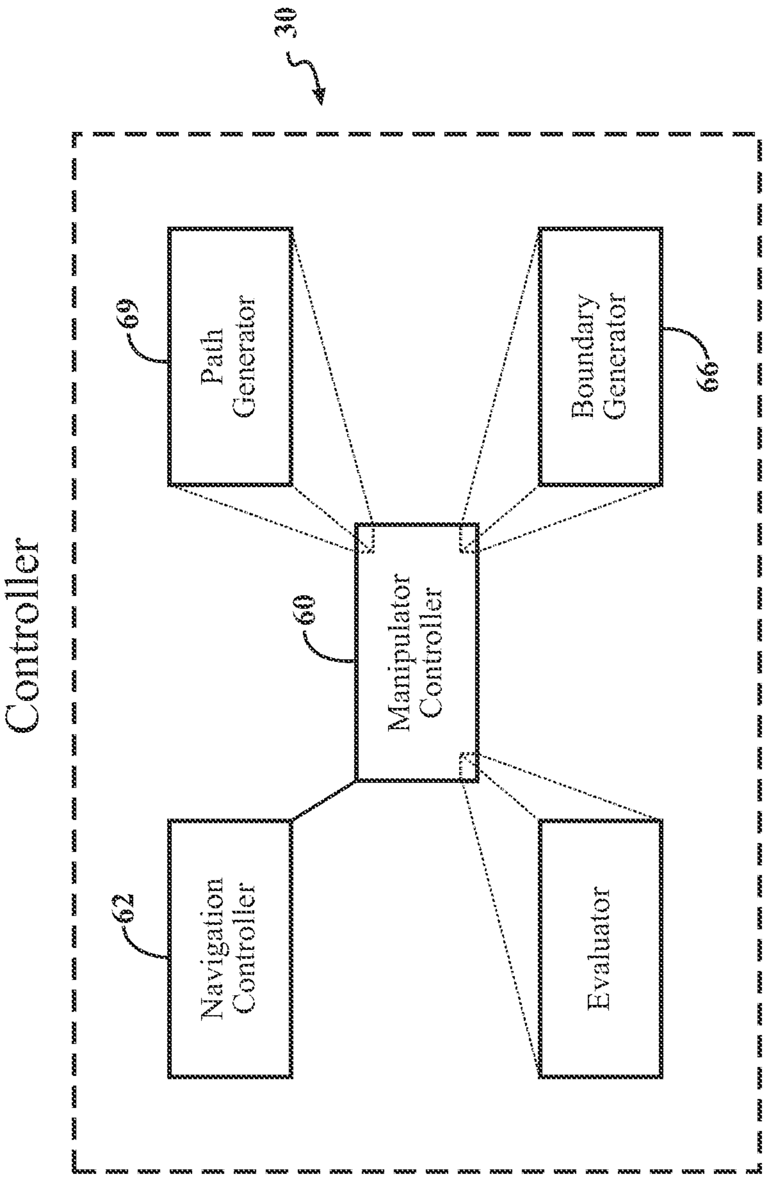
FIG. 2 is a block diagram of a controller that may be used with the system shown in FIG. 1.

Referring to FIG. 2, the system 10 includes a controller 30. The controller 30 includes software and/or hardware for controlling the manipulator 14. The controller 30 directs the motion of the manipulator 14 and controls an orientation of the end effector 20 with respect to a coordinate system. In one embodiment, the coordinate system is a manipulator coordinate system MNPL (see FIG. 1). The manipulator coordinate system MNPL has an origin, and the origin is located at a point on the manipulator 14. One example of the manipulator coordinate system MNPL is described in U.S. Pat. No. 9,119,655, entitled, "Surgical Manipulator Capable of Controlling a Surgical Instrument in Multiple Modes," the disclosure of which is hereby incorporated by reference.

The system 10 further includes a navigation system 32. One example of the navigation system 32 and components related thereto is described in U.S. Pat. No. 9,008,757, filed on Sep. 24, 2013, entitled, "Navigation System Including Optical and Non-Optical Sensors," hereby incorporated by reference. The navigation system 32 is set up to track movement of various objects. Such objects include, for example, the end effector 20, and the anatomy or portions thereof, e.g., femur F, tibia T, and acetabulum (not shown). The navigation system 32 tracks these objects to gather position information of each object in a localizer coordinate system LCLZ. Coordinates in the localizer coordinate system LCLZ may be transformed to the manipulator coordinate system MNPL using conventional transformation techniques. The navigation system 32 is also capable of displaying a virtual representation of their relative positions and orientations to the operator.

The navigation system 32 includes a computer cart assembly 34 that houses a navigation computer 36, and/or other types of control units. A navigation interface is in operative communication with the navigation computer 36. The navigation interface includes one or more displays 38. First and second input devices 40, 42 such as a keyboard and mouse or touch screen may be used to input information into the navigation computer 36 or otherwise select/control certain characteristics of the navigation computer 36. Other input devices 40, 42 are contemplated including voice-activation. The controller 30 may be implemented on any suitable device or devices in the system 10, including, but not limited to, the manipulator computer 26, the navigation computer 36, and any combination thereof.

The navigation system 32 also includes a localizer 44 that communicates with the navigation computer 36. In one embodiment, the localizer 44 is an optical localizer and includes a camera unit 46. The camera unit 46 has an outer casing 48 that houses one or more optical position sensors 50. The system 10 includes one or more trackers. The trackers may include a pointer tracker PT, a tool tracker 52, a first patient tracker 54, and a second patient tracker 56. The trackers include markers 58. The markers 58 may be light emitting diodes or LEDs. In other embodiments, the markers 58 are passive markers, such as reflectors, which reflect light emitted from the camera unit 46. Those skilled in the art appreciate that other suitable tracking systems and methods not specifically described herein may be utilized, such as electromagnetic localization systems, ultrasound, and the like.

In the illustrated embodiment of FIG. 1, the first patient tracker 54 is firmly affixed to the femur F of the patient 12 and the second patient tracker 56 is firmly affixed to the tibia T of the patient 12 for use in a knee replacement surgery, for example. Alternatively, the first patient tracker 54 may be affixed to the femur F of the patient 12 and the second patient tracker 56 may be affixed to an acetabulum or pelvis of the patient 12 for use in a hip replacement surgery. The patient trackers 54, 56 are firmly affixed to sections of bone. The tool tracker 52 is firmly attached to the end effector 20. It should be appreciated that the trackers 52, 54, 56 may be fixed to their respective components in any suitable manner.

The trackers 52, 54, 56 communicate with the camera unit 46 to provide position data to the camera unit 46. The camera unit 46 provides the position data of the trackers 52, 54, 56 to the navigation computer 36. In one embodiment in which trackers 54 and 56 are coupled to the femur F and acetabulum of the patient, the navigation computer 36 determines and communicates position data of the femur F and acetabulum and position data of the end effector 20 to the manipulator computer 26. Alternatively, the navigation computer 36 may determine position data of the tibia T or another portion of the anatomy to which tracker 56 may be coupled and may communicate the position data to the manipulator computer 26. Position data for the femur F, acetabulum, and end effector 20 may be determined by the tracker position data using conventional registration/navigation techniques. The position data includes position information corresponding to the position and/or orientation of the femur F, acetabulum, end effector 20 and any other objects being tracked. The position data described herein may be position data, orientation data, or a combination of position data and orientation data.

The manipulator computer 26 transforms the position data from the localizer coordinate system LCLZ into the manipulator coordinate system MNPL by determining a transformation matrix using the navigation-based data for the end effector 20 and encoder-based position data for the end effector 20. Encoders (not shown) located at joints of the manipulator 14 are used to determine the encoder-based position data. The manipulator computer 26 uses the encoders to calculate an encoder-based position and orientation of the end effector 20 in the manipulator coordinate system MNPL. Since the position and orientation of the end effector 20 are also known in the localizer coordinate system LCLZ, the transformation matrix may be generated.

As shown in FIG. 2, the controller 30 further includes software modules. The software modules may be part of a computer program or programs that operate on the manipulator computer 26, navigation computer 36, or a combination thereof, to process data to assist with control of the system 10. The software modules include sets of instructions stored in memory on the manipulator computer 26, navigation computer 36, or a combination thereof, to be executed by one or more processors of the computers 26, 36. Additionally, software modules for prompting and/or communicating with the operator may form part of the program or programs and may include instructions stored in memory on the manipulator computer 26, navigation computer 36, or a combination thereof. The operator interacts with the first and second input devices 40, 42 and the one or more displays 38 to communicate with the software modules.

In one embodiment, the controller 30 includes a manipulator controller 60 for processing data to direct motion of the manipulator 14. The manipulator controller 60 may receive and process data from a single source or multiple sources.

The controller 30 further includes a navigation controller 62 for communicating the position data relating to the femur F, acetabulum (or other portions of the anatomy such as the tibia T), and end effector 20 to the manipulator controller 60. The manipulator controller 60 receives and processes the position data provided by the navigation controller 62 to direct movement of the manipulator 14. In one embodiment, as shown in FIG. 1, the navigation controller 62 is implemented on the navigation computer 36.

The manipulator controller 60 or navigation controller 62 may also communicate positions of the patient 12 and end effector 20 to the operator by displaying an image of the anatomy (e.g., acetabulum and/or femur F) and the end effector 20 on the display 38. The manipulator computer 26 or navigation computer 36 may also display instructions or request information on the display 38 such that the operator may interact with the manipulator computer 26 for directing the manipulator 14.

The manipulator 14 autonomously interacts with the anatomy. Specifically, the system 10 may include a semi-autonomous mode, an example of which is described in U.S. Pat. No. 9,119,655, entitled, "Surgical Manipulator Capable of Controlling a Surgical Instrument in Multiple Modes," the disclosure of which is hereby incorporated by reference. In the semi-autonomous mode, the manipulator 14 directs autonomous movement of the end effector 20 and, in turn, the energy applicator 24 at the surgical site. The manipulator 14 is capable of moving the end effector 20 free of operator assistance. Free of operator assistance may mean that an operator does not physically contact the end effector 20 to apply force to move the end effector 20. Instead, the operator may use some form of control to remotely manage starting and stopping of movement. For example, the operator may hold down a button of a remote control to start movement of the end effector 20 and release the button to stop movement of the end effector 20. Alternatively, the operator may press a button to start movement of the end effector 20 and press a button to stop movement of the end effector 20.

Figure 3:
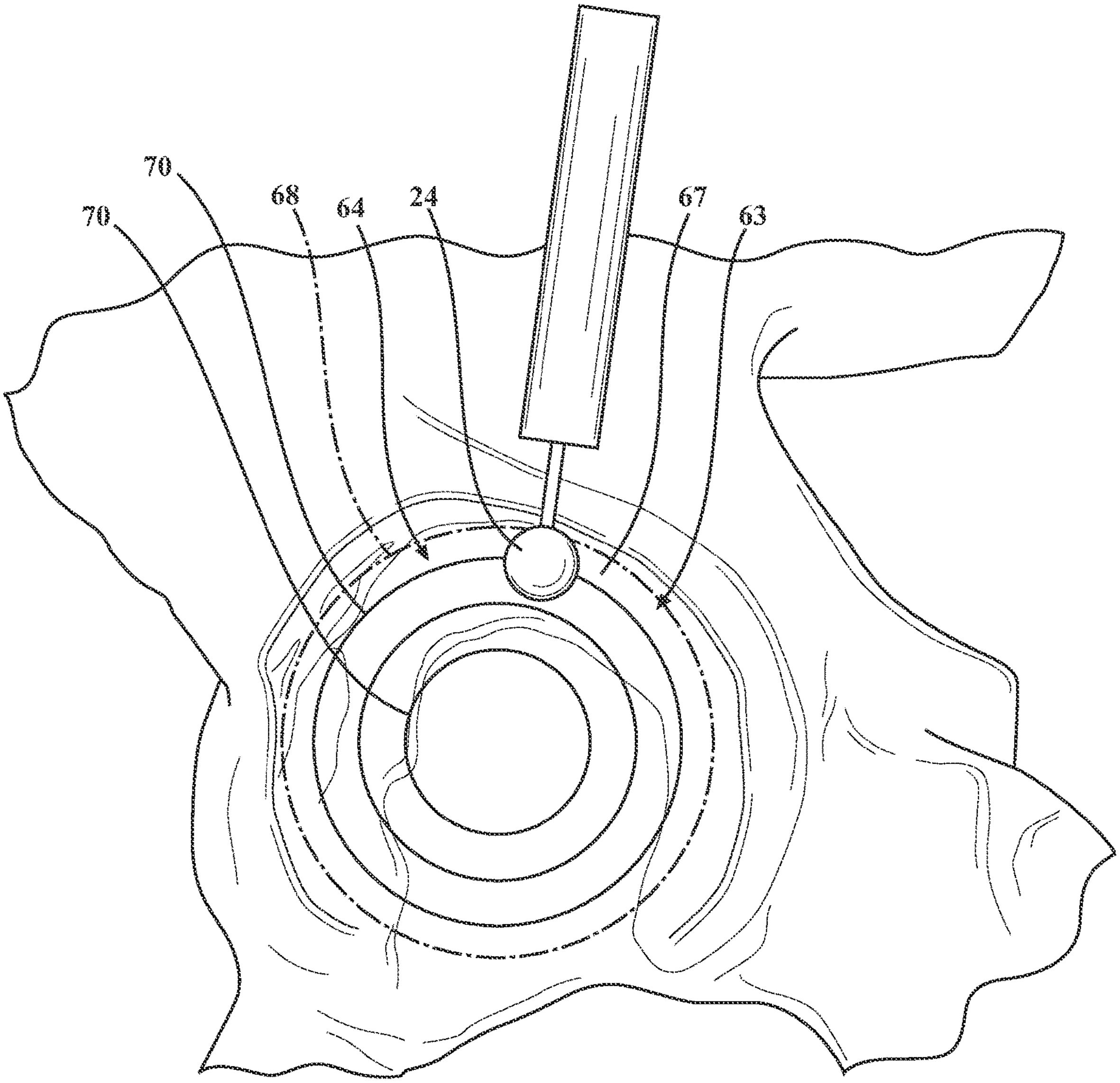
FIG. 3 is a perspective view of a portion of an anatomy and a tool for manipulating the anatomy.

The controller 30 is configured to generate manipulation parameters 63 in relation to a volume 64 of the anatomy, as shown in FIG. 3. The manipulation parameters 63 represent planned constraints on autonomous manipulation of the volume 64 by the energy applicator 24 of the end effector 20. As described below, the manipulation parameters 63 may include virtual cutting boundaries, tool cutting paths, or any combination thereof. The manipulation parameters 63 are defined to promote manipulation, removal, and/or cutting of the volume 64 of the anatomy. The manipulation parameters 63 are executed in a first mode. In one embodiment, the first mode may be understood to be a "manipulation" or "cutting" mode. Therefore, for simplicity, the first mode is hereinafter referred to as the manipulation mode in the detailed description.

As shown in FIG. 2, the controller 30 includes a boundary generator 66 for generating the manipulation parameters 63. The boundary generator 66 is a software module that may be implemented on the manipulator controller 60, as shown in FIG. 2. Alternatively, the boundary generator 66 may be implemented on other components, such as the navigation controller 62.

As shown in FIG. 3, the boundary generator 66 generates a cutting boundary 68 for constraining the end effector 20 and/or energy applicator 24 in relation to the anatomy. The cutting boundary 68 is a virtual boundary in that the boundary is not physically present, but rather is implemented by controlling position and movement of the manipulator 14 and the end effector 20. The cutting boundary 68 delineates sections of tissue to be removed by the end effector 20 during the surgery from sections of tissue that are to remain after the surgery. As shown in FIG. 3, the cutting boundary 68 is associated with the anatomy, and more specifically a target surface 67 of the anatomy. The cutting boundary 68 is defined in relation to the target surface 67. The target surface 67 is a contiguous defined surface area of the tissue that is to remain after cutting has completed. For implant procedures, the target surface 67 is the surface of the bone remaining after the removal procedure and is the surface to which the implant is to be mounted. In one embodiment, the implant is mounted to the target surface 67 using bone cement, such as polymethylmethacrylate (PMMA) bone cement, or another suitable adhesive or mechanism. The cutting boundary 68 may have a profile that substantially conforms to the target surface 67.

During the procedure, the cutting boundary 68 may be slightly offset or spaced apart from the target surface 67. In one embodiment, this is done to account for the size and manipulation characteristics of the energy applicator 24 of the end effector 20. The manipulation characteristics of the end effector 20 may cause a breaching of the cutting boundary 68. To account for this overreaching, the cutting boundary 68 may be translated from target surface 67 by a predetermined distance defined between the target surface

67 and the cutting boundary 68. Those skilled in the art understand that the cutting boundary 68 may have other configurations not specifically described herein and may be configured or oriented in relation to the anatomy according to other embodiments not shown or described.

The cutting boundary 68 may be derived from various inputs to the manipulator 14, and more specifically, the boundary generator 66. One input into the boundary generator 66 includes preoperative images of the site on which the procedure is to be performed. If the manipulator 14 selectively removes tissue so the patient 12 may be fitted with an implant, a second input into the boundary generator 66 is a map of the shape of the implant. The initial version of this map may come from an implant database. The shape of the implant may at least partially define the boundaries of the tissue that should be removed to receive the implant. This relationship is especially true if the implant is an orthopedic implant intended to be fitted to the bone of the patient 12. Additionally or alternatively, the boundaries of the tissue to be removed may be at least partially defined by a cement or adhesive used to secure the implant to the anatomy as described herein. Images of the anatomy may be segmented to create a computer-generated model of the anatomy. The manipulation parameters 63 may be generated based on the computer-generated model of the anatomy. More specifically, the cutting boundary 68 may be generated in relation to the computer-generated model.

Another input into boundary generator 66 may include adhesive settings. These settings may indicate a thickness of adhesive that is planned to be used to secure the implant to the target surface 67 and a geometry of the target surface 67 that is desired for optimal bonding of the adhesive to the target surface 67. Accordingly, in embodiments in which an adhesive is used to secure the implant to the target surface 67, the cutting boundary 68 may be defined based on the geometry of the implant, the desired thickness of adhesive, and the geometry of the desired bonding area of the target surface 67.

Another input into boundary generator 66 is the operator settings. These settings may indicate to which tissue the energy applicator 24 should be applied. If the energy applicator 24 removes tissues, the settings may identify the boundaries between the tissue to be removed and the tissue that remains after application of the energy applicator 24. If the manipulator 14 assists in the fitting of an orthopedic implant, these settings may define where over the tissue the implant should be positioned. These settings may be entered preoperatively using a data processing unit. Alternatively, these settings may be entered through an input/output unit associated with one of the components of the system 10 such as with navigation interface 40, 42.

Based on the above input data and instructions, boundary generator 66 may generate the cutting boundary 68. The cutting boundary 68 may be two-dimensional or three-dimensional. For example, the cutting boundary 68 may be generated as a virtual map or other three-dimensional model. The created maps or models guide movement of the end effector 20. The models may be displayed on displays 38 to show the locations of the objects. Additionally, information relating to the models may be forwarded to the manipulator controller 60 to guide the manipulator 14 and corresponding movement of the end effector 20 relative to the cutting boundary 68.

In practice, prior to the start of the procedure the operator at the surgical site may set an initial version of the cutting boundary 68 based on the inputs to the boundary generator 66 described above. At the start of the procedure, data that more precisely defines the implant that is to be actually fitted to the patient 12 may be loaded into the boundary generator 66. Such data may come from a storage device associated with the implant such as a memory stick or an RFID tag. Such data may be a component of the implant database data supplied to the boundary generator 66. These data are based on post manufacture measurements of the specific implant. These data provide a definition of the shape of the specific implant that, due to manufacturing variations, may be slightly different than the previously available stock definition of implant shape. Based on this implant-specific data, the boundary generator 66 may update the cutting boundary 68 to reflect the boundaries between the tissue to be removed and the tissue that should remain in place. Implants that could be implanted into the patient 12 include those shown in U.S. Pat. No. 9,381,085 and entitled, "Prosthetic Implant and Method of Implantation", hereby incorporated by reference. The implants disclosed herein could be implanted in the patient 12 after the appropriate amount of material, such as bone, is removed based on the cutting boundary 68 defined above. Other implants are also contemplated.

As shown in FIG. 2, the controller 30 further includes a tool path generator 69 for generating manipulation parameters 63. The tool path generator 69 is another software module run by the controller 30, and more specifically, the manipulator controller 60. The tool path generator 69 generates a cutting path 70 for the end effector 20 to follow, as shown in FIG. 3. The cutting path 70 is represented by concentric circles penetrating into the bone. In FIG. 3, the cutting path 70 is configured to facilitate removal of the volume 64 of bone which is to be removed to receive the implant. The smoothness and quality of the finished surface depends in part on the relative positioning of the cutting paths. More specifically, the closer together each pass is, the more precise and smooth is the finished surface. Although shown as a series of concentric circular cutting paths, it will be understood by one of skill in the art that other paths may be used, such as a back-and-forth configuration.

In FIG. 3, the dashed line represents the cutting boundary 68 for constraining the end effector 20 and/or energy applicator 24 in relation to the bone that is to be removed using manipulator 14. One exemplary system and method for generating the cutting path 70 is explained in U.S. Pat. No. 9,119,655, entitled, "Surgical Manipulator Capable of Controlling a Surgical Instrument in Multiple Modes," the disclosure of which is hereby incorporated by reference.

Figure 4:
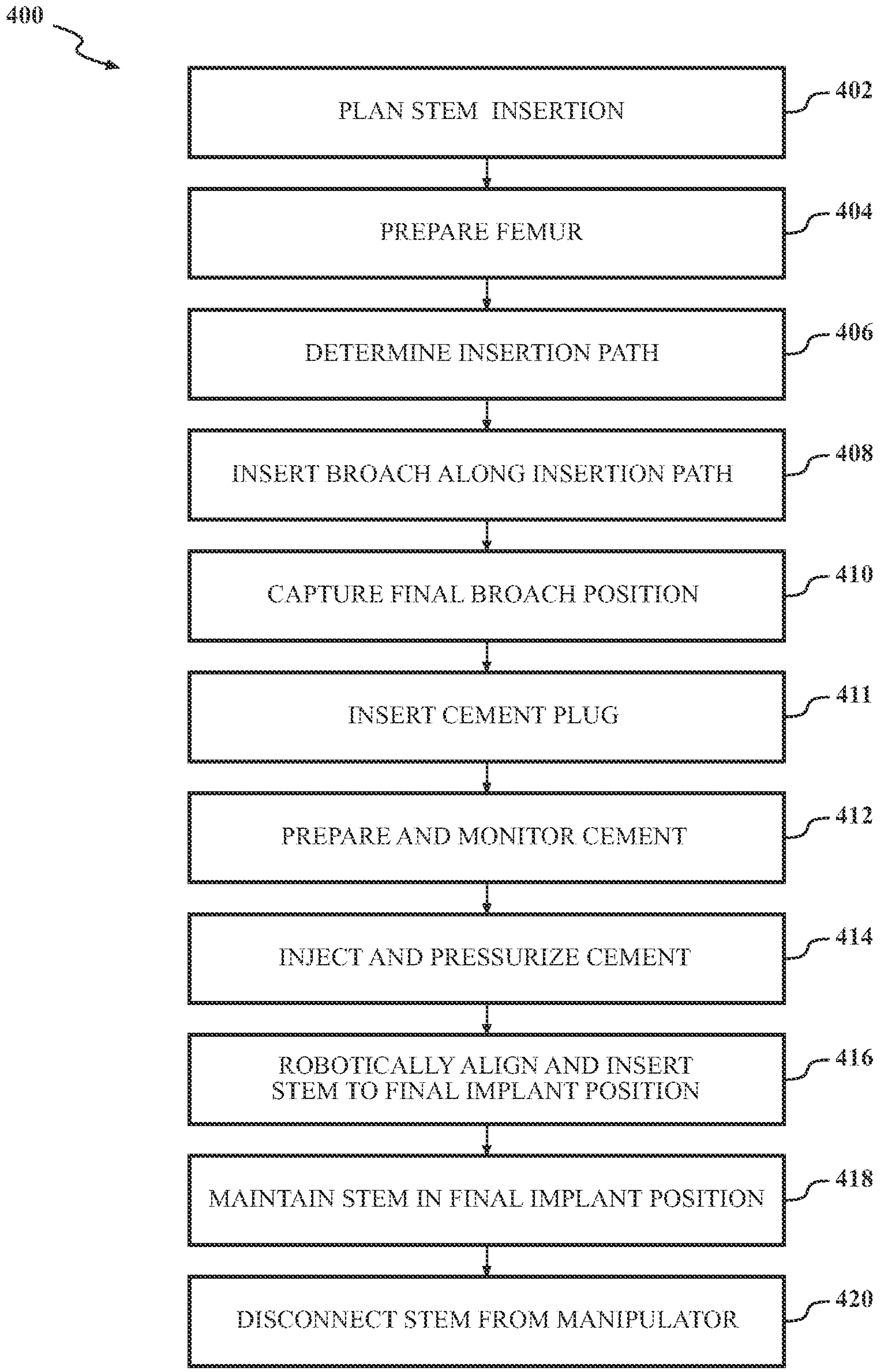
FIG. 4 is a flowchart of a method of robotically assisting a surgical procedure.

FIG. 4 is a flow diagram of an exemplary method 400 of robotically assisting a surgical procedure, such as a hip replacement procedure, that may be used with system 10 (shown in FIG. 1). More specifically, FIG. 4 illustrates a method 400 for planning and inserting an implant into a patient's femur as part of the hip replacement procedure. While FIG. 4 describes portions of a robotically assisted hip replacement procedure, it should be recognized that aspects of method 400 may alternatively be used with other surgical procedures, such as a knee replacement procedure or any other suitable surgical procedure. Further details of each step of method 400 are described with reference to FIGS. 6-14.

In an exemplary embodiment, method 400 includes planning 402 an insertion of a femoral stem into a portion of a patient's anatomy, such as a femur, in preparation for the hip replacement procedure. The femur is prepared 404 for the insertion of the implant (i.e., femoral stem), and an insertion path is determined 406 for the stem. One or more broaches or other cavity creation tools are inserted 408 along the insertion path to create a cavity in the femur for receiving the femoral stem implant. For example, in one embodiment, a bur or other end effector 20 may be used to create the cavity in the femur in preparation for receiving the femoral stem implant. When the broach has reached the desired insertion depth and orientation, a final broach position is captured 410 using localizer 44, for example.

In an embodiment in which the femoral stem implant is cemented into the cavity formed in the femur by the broach (or series of broaches), a cement plug or seal may be manually or robotically inserted 411 or placed over the mouth of the femoral cavity. A predetermined amount of bone cement may be prepared 412 and monitored. Once the cement has reached a desired viscosity or when a predetermined amount of time has elapsed, the cement is injected 414 into the cavity and is pressurized to facilitate the securing of the cement to the femoral bone surrounding the cavity. For example, in one embodiment, manipulator controller 60 may measure the viscosity of the bone cement and may inject the bone cement into the cavity when the viscosity has reached a predetermined value or threshold. Alternatively, the cement or other adhesive may be delivered into the cavity by mixing two or more pastes within a nozzle or other portion of a cement injection apparatus. The cement may be injected into the cavity through a hole in the plug or seal, or the cement may be injected first and the plug or seal may be placed over the mouth of the cavity after the cement or adhesive is injected.

The stem is connected to the manipulator 14, then robotically aligned and inserted 416 to the final implant position (e.g., the final broach position or the final implant position defined during the planning phase). The stem is maintained or secured 418 in the final implant position until the cement has cured or polymerized. After a predetermined amount of time has elapsed, the stem is disconnected 420 from the robotic manipulator.

It should be recognized that each of the steps of method 400 may be performed in an automatic, autonomous, or semi-autonomous manner by manipulator 14 as described more fully with reference to FIGS. 6-14. Alternatively, the steps may be performed manually by a surgeon with assistance from manipulator 14 and/or using other surgical tools, or may be performed using any combination thereof.

Figure 5:
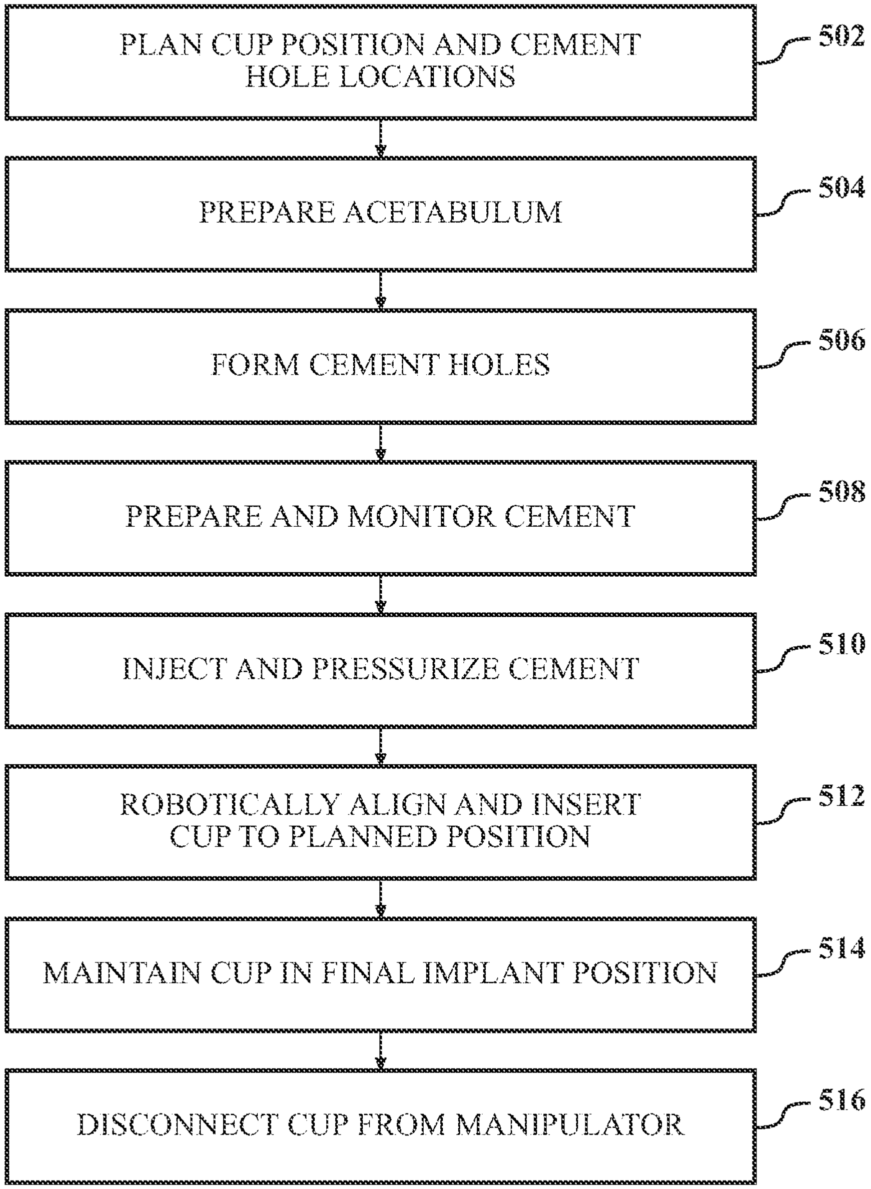
FIG. 5 is a flowchart of another method of robotically assisting a surgical procedure.

FIG. 5 is a flow diagram of another exemplary method 500 of robotically assisting a surgical procedure, such as a hip replacement procedure, that may be used with system 10 (shown in FIG. 1). More specifically, FIG. 5 illustrates a method 500 for planning and inserting an implant into a patient's acetabulum as part of the hip replacement procedure in cooperation with method 400 (shown in FIG. 4). While FIG. 5 describes portions of a robotically assisted hip replacement procedure, it should be recognized that aspects of method 500 may alternatively be used with other surgical procedures, such as a knee replacement procedure or any other suitable surgical procedure. Further details of each step of method 500 are described with reference to FIGS. 15-20.

In an exemplary embodiment, method 500 includes planning 502 an acetabular cup implant to receive a head of a femoral stem implant such as described above with reference to FIG. 4. The planning 502 of the acetabular cup implant includes planning a position and orientation of a cavity to receive the acetabular cup within the acetabulum and planning the location and orientation of a plurality of cement holes to be formed within the acetabular cavity for receiving bone cement.

The acetabulum is prepared 504 to receive the acetabular cup implant by reaming, using a bur, or otherwise removing bone and osteophytes to form the planned cavity. The planned number and arrangement of cement holes are drilled or otherwise formed 506 by an energy applicator, for example, attached to the manipulator or by a powered drill or other tool operated by the surgeon.

In an embodiment in which the acetabular cup implant is cemented into the cavity formed in the acetabulum, a predetermined amount of bone cement is prepared and monitored 508. Once the cement has reached a desired viscosity or when a predetermined amount of time has elapsed, the cement is injected into the cavity and is pressurized 510 to facilitate the securing of the cement to the acetabular bone surrounding the cavity. For example, in one embodiment, manipulator controller 60 may measure the viscosity of the bone cement and may inject the bone cement into the cavity when the viscosity has reached a predetermined value or threshold. Alternatively, the cement or other adhesive (e.g., PMMA bone cement) may be delivered into the cavity by mixing two or more pastes within a nozzle or other portion of a cement injection apparatus.

The acetabular cup is robotically aligned and inserted 512 into the planned implant position within the cavity. The acetabular cup is maintained or secured 514 in the final implant position until the cement has cured or polymerized. After a predetermined amount of time has elapsed, the acetabular cup is disconnected 516 from the robotic manipulator. For example, the acetabular cup may be secured to the pelvis until the cement has cured or polymerized. The acetabular cup may also be automatically maintained in position relative to the pelvis even if the patient moves by causing the acetabular cup to automatically match the movement of the pelvis (e.g., by automatically moving end effector 20 to which the acetabular cup is attached) as described more fully herein. Alternatively, the acetabular cup may be released after it has been placed in the final implant position, and the surgeon may manually maintain the acetabular cup in position until the cement has cured or polymerized.

It should be recognized that each of the steps of method 500 may be performed in an automatic, autonomous, or semi-autonomous manner by the manipulator 14 as described more fully with reference to FIGS. 15-20. Alternatively, the steps may be performed manually by a surgeon with assistance from the manipulator 14 and/or using other surgical tools, or may be performed using any combination thereof.

Figure 6:
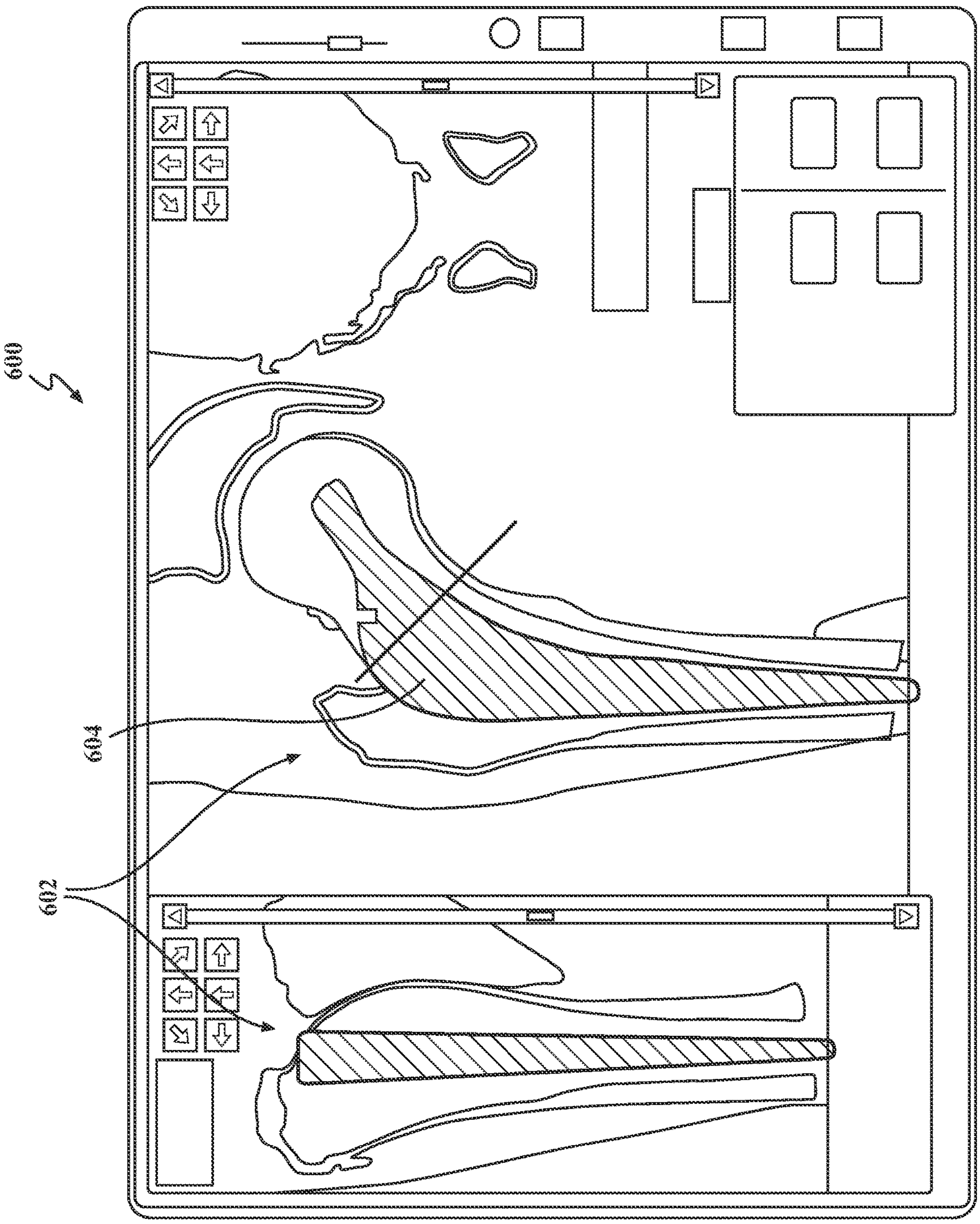
FIG. 6 is an image of a portion of a patient's anatomy into which an implant is planned to be inserted.

FIG. 6 is an image of a portion of a patient's anatomy into which an implant is planned to be inserted. Specifically, FIG. 6 illustrates an x-ray image 600 of a portion of a patient's femur 602 and an outline of a femoral stem 604 that is planned to be inserted into femur 602. FIG. 6 illustrates part of planning an insertion of a femoral stem into a portion of a patient's anatomy referenced by step 402 of method 400 (shown in FIG. 4). While FIG. 6 is described with reference to x-ray images, it should be recognized that other imaging modalities may be used instead, such as MRI, CT scan, ultrasound, etc. In addition, the images may be two-dimensional (2D), three-dimensional (3D), or a combination thereof (e.g., biplanar x-ray imaging).

In one embodiment, the outline of stem 604 is computer-generated and superimposed on the image of femur 602 to assist a surgeon in planning the location and dimensions of the implant. The surgeon may select a stem 604 having a desired size from a predefined list or catalog of stem sizes to achieve an optimal fit within image 600 and to achieve an optimal planned leg length, for example, for the patient.

In one embodiment, navigation system 32 displays image 600 on display 38 and displays the computer-generated image of the selected femoral stem implant within image 600 on display 38. The surgeon determines the appropriate size of femoral stem 604 that will enable a desired amount of bone surrounding stem 604 to provide a suitable and stable support for the implant and to achieve desired leg length for the patient. The size and placement of the planned stem 604 takes into account a planned thickness of cement that is to be injected into a cavity defined in femur 602 to secure stem 604 within femur 602.

Once the surgeon has selected the final implant size and final planned position for the implant, navigation system 32 translates the position and orientation of the planned stem position into the localizer coordinate system LCLZ in preparation for determining the planned insertion path of the femoral stem implant.

Figure 7:
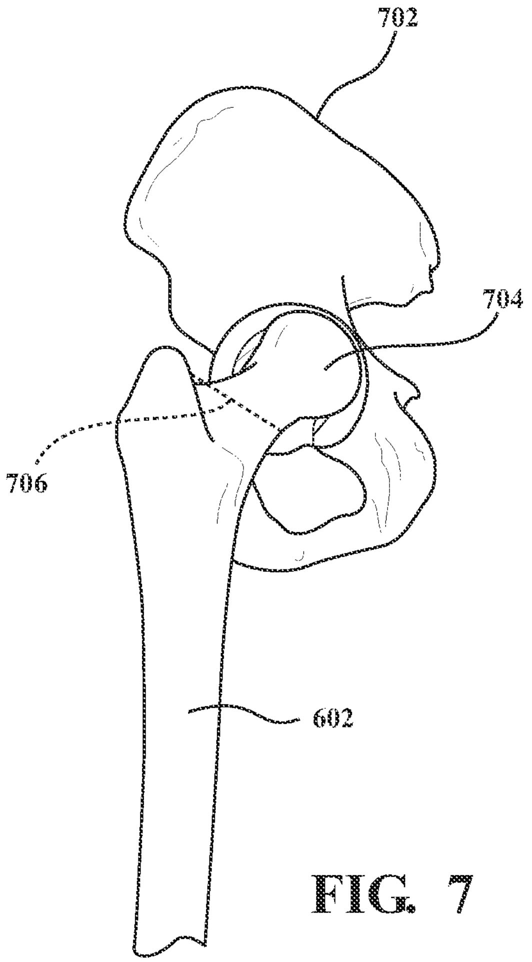
FIG. 7 is a perspective view of a portion of a patient's anatomy.

FIG. 7 is a perspective view of a portion of a patient's femur 602 and pelvis 702 used to illustrate the preparation of the femur as set forth in step 404 of method 400 (shown in FIG. 4).

During the femoral preparation step, a head 704 of the femur 602 is removed along a femoral neck resection line 706. The angle and position of femoral neck resection line 706 may be calculated during the planning step 402 of method 400 and may be stored in a memory of navigation computer 36 or another suitable storage device. During the surgical procedure to remove the femoral head 704, navigation controller 62 or another suitable controller may reference the planned femoral neck resection line angle and position and translate the angle and position to the manipulator coordinate system MNPL.

Once the angle and position of the femoral neck resection line 706 has been translated or otherwise determined, manipulator may operate end effector 20 and energy applicator 24 to automatically cut through the femur 602 along the femoral neck resection line 706. Localizer 44 may continually track the position of the patient's femur 602, end effector 20, and/or energy applicator 24 and may transmit real-time position data to manipulator controller 60 through navigation controller 62. Manipulator controller 60 may use the real-time position data, encoder data, and/or data representing the femoral neck resection line 706 angle and position to ensure that energy applicator 24 does not deviate from line 706.

More specifically, in one embodiment, path generator 69 may create a movement path for energy applicator 24 (e.g., a saw blade) that mirrors the femoral neck resection line 706. Navigation controller 62 may track the position of end effector 20 via signals received from localizer 44 and may transmit the position data to manipulator controller 60. Manipulator controller 60 may automatically guide energy applicator 24 along the movement path based on the position data and/or encoder data while energy applicator 24 is operating (i.e., cutting or drilling) to cause energy applicator 24 to cut through or otherwise remove the bone along femoral neck resection line 706.

Alternatively, the head 704 of the femur 602 may be removed by a surgeon operating a hand tool such as a saw or drill, or by the surgeon operating end effector 20 and energy applicator 24 in a manual mode. The manual mode may include a haptics-based mode in which manipulator controller 60 prevents the surgeon from deviating from femoral neck resection line 706 or generates a haptics-based alert, such as a vibration, to the surgeon if the surgeon deviates from femoral neck resection line 706. Alternatively or additionally, the manual mode may include a navigated mode in which the progress of the femoral neck resection is displayed on display 38 so that the surgeon can visually identify how the resection is tracking the planned femoral neck resection line 706. In each of the haptics-based and navigated modes, the position of the portion of the patient's anatomy that the surgeon is operating on (i.e., the femur in this case) and the position of the end effector 20 and/or energy applicator 24 may be tracked in real-time by localizer 44 and may be displayed on display 38 and/or may be communicated to manipulator controller 60 via navigation controller 62.

After resection, the proximal end of femur 602 may be opened with a bur or other tool operated by the surgeon under haptic control, or may be opened automatically via energy applicator 24 in preparation for creating a cavity in femur 602.

Figure 8:
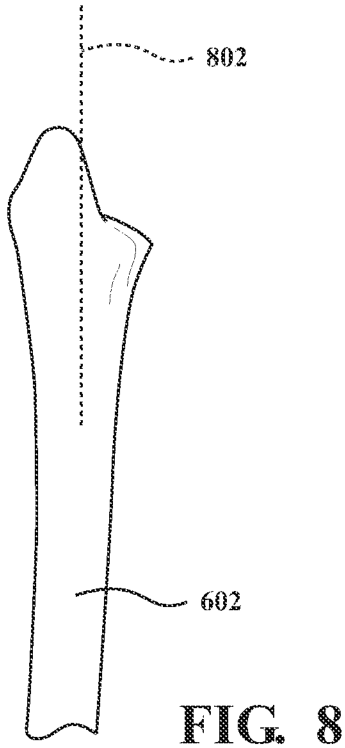
FIG. 8 is a side view of a portion of the patient's anatomy to illustrate the step of determining an insertion path for an implant for the surgical procedure shown in FIG. 4.

FIG. 8 is a side view of a portion of the patient's anatomy (i.e., femur 602) used to illustrate the step of determining 406 an insertion path for an implant used with method 400 (shown in FIG. 4).

In one embodiment, a planned insertion path for the implant is initially determined in the planning step 402 to ensure that a desired thickness of bone cement will surround the implant in the cavity when the implant is inserted to its final implant position. The planned implant insertion path is used to determine a path for creating a cavity using one or more cavity creation tools and to determine a path for an implant to be inserted into the cavity created in the portion of the patient's anatomy (e.g., the femur). In one embodiment, the implant insertion path ends at a final implant position which corresponds to the final position of the cavity creation tool after the cavity creation tool has completed forming the cavity. Alternatively, the final implant position corresponds to the planned position of the implant that was determined during the planning phase.

Path generator 69 may create an insertion path 802 for the implant to follow during the surgical procedure based on the planned insertion path determined above and/or based on the desired final implant position. In one embodiment, path generator 69 receives and uses data representative of the geometry and dimensions of the implant selected during the planning phase when determining insertion path 802 for the implant. For example, if the implant selected to be inserted into the patient's femur 602 has a substantially straight centerline axis, implant insertion path 802 may be created having a substantially straight path to reduce or eliminate a formation of cement voids that may otherwise be created during the insertion of the implant. Conversely, if the implant selected to be inserted into the patient's femur 602 has a curved centerline axis, implant insertion path 802 may be created having a curved path to reduce or eliminate cement voids. The insertion path may also be modified based on the specific surgical approach. For example, if the surgeon is performing a direct anterior approach, a curved insertion path may be selected. In another example, a curved insertion path 802 may be used with an implant having a straight centerline axis to enable a surgeon to avoid soft tissue structures, after which the surgeon may straighten or align the implant to the final implant position.

Boundary generator 66 may generate one or more boundaries for implant insertion path 802 to prevent a surgeon or the manipulator from deviating from implant insertion path 802 during the surgical procedure.

Figure 9:
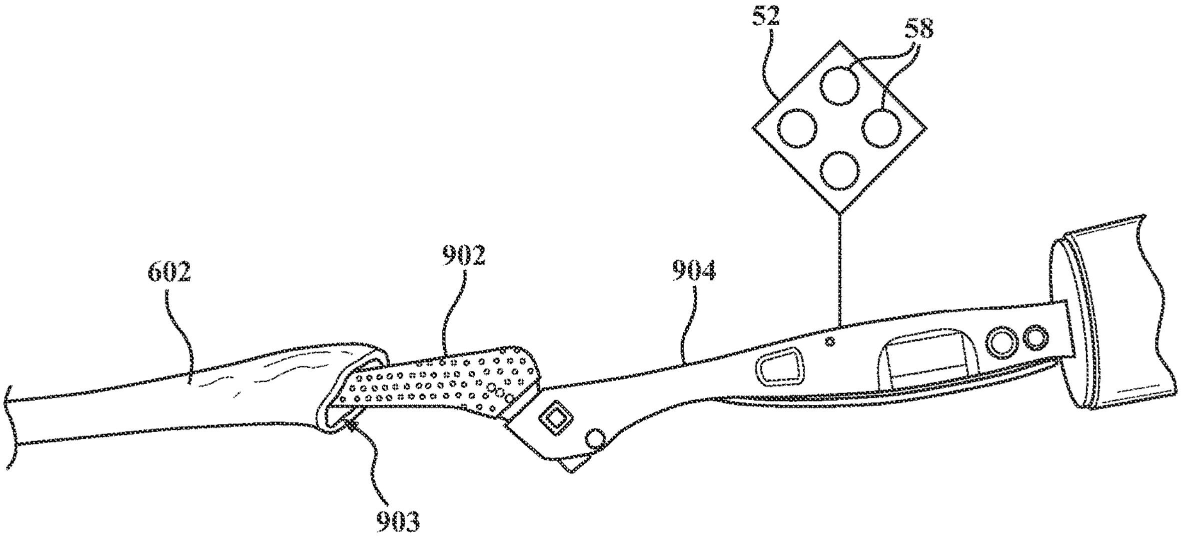
FIG. 9 is a perspective view of a portion of a patient's anatomy to illustrate the step of inserting a cavity creation tool along a determined insertion path for the surgical procedure shown in FIG. 4.

FIG. 9 is a perspective view of a portion of a patient's anatomy (i.e., femur 602) that may be used to illustrate the step of inserting 408 a cavity creation tool 902, such as a broach 902, along the determined insertion path that may be used with method 400 (shown in FIG. 4).

In one embodiment, cavity creation tools 902 may include one or more rasps, broaches, trochars, burs, drills, reamers, or the like that may be used to form a cavity 903 within the portion of the patient's anatomy. The cavity 903 is formed to receive the implant and any mechanisms for securing the implant to the portion of the patient's anatomy, such as bone cement or other suitable anchors. While the following description relates to inserting one or more broaches 902 into a patient's femur 602 as part of a hip replacement procedure, it should be recognized that any suitable cavity creation tool may be used to create a cavity 903 or otherwise prepare any suitable portion of a patient's anatomy for implant insertion.

As described herein, one or more broaches 902 are used as cavity creation tools to create and develop the cavity 903 within the patient's femur 602. In one embodiment, manipulator 14 may automatically insert broach 902 into the femur 602 along insertion path 802, for example, using an end effector 20 adapted for use therein. For example, end effector 20 may include a mounting portion 904 onto which broach 902 is removably attached. The broach 902 may be removably attached to end effector 20 by a releasable bayonet connection, a friction fit connection that can be released by end effector 20 moving away from broach 902 at a predetermined angle, a releasable pin mechanism, or by any other suitable connection.

End effector 20 may singly or repeatedly drive the broach into femur 602 to create and develop the cavity 903, for example, using a motorized or hydraulic impactor. The cavity 903 may be progressively developed by increasing the depth and width of the cavity 903, for example, through successive insertions of the broach 902 and/or through successive insertions of broaches 902 of increasing size. In such an embodiment, manipulator 14 may monitor the insertion force of the broach 902 using a pressure sensor attached to end effector 20 or attached to another suitable portion of manipulator 14 or broach 902. The manipulator 14 may compare the measured impact pressure to a threshold value to prevent the insertion force from exceeding the threshold value.

Manipulator 14 may reference insertion path 802 and any boundaries created by boundary generator 66 to ensure that the insertion of broach or broaches 902 does not deviate from insertion path 802 by a predetermined amount. For example, manipulator controller 60 may use position data received from navigation controller 62 based on tracking of the broach 902 via a tracker 52 attached to the mounting portion 904 of the end effector 20 and/or encoder data from the manipulator 14. A known relationship between the tracker 52 and each broach 902 may be separately stored in the controller 30 for access by the navigation controller 62 to determine a position and/or orientation of each broach 902 successively inserted. Path data from path generator 69 and boundary data from boundary generator 66 are also used to insert the broach 902 along the insertion path 802.

In one embodiment, the surgeon may use manipulator 14 in a haptics-based or navigated mode in which manipulator controller 60 (using signals received from localizer 44 and/or encoder data) prevents the insertion of the broach 902 from deviating from the insertion path 802 by a predetermined amount or alerts the surgeon if the insertion of the broach 902 deviates from the insertion path 802 by a predetermined amount.

Alternatively, the surgeon may use a broach 902 that is removably attached to end effector 20 and the surgeon can manually operate the end effector 20 to insert the broach 902 using a haptics-based mode or a navigated mode of manipulator 14. Localizer 44 and/or the manipulator 14 tracks the position of end effector 20 and/or the broach 902 as well as the position of the patient's femur 602 and transmits the position data to manipulator controller 60 via navigation controller 62. If manipulator controller 60 detects that the surgeon is attempting to insert broach 902 at an angle that is different than the angle of insertion path 802, manipulator controller 60 may either prevent the movement of end effector 20 (and broach 902 attached thereto) along the erroneous path and/or may provide haptic feedback to the surgeon through end effector 20 to indicate that the angle and/or insertion path 802 that the surgeon is attempting to use to insert the broach 902 is incorrect. Additionally or alternatively, the real-time position data of the femur 602 and the end effector 20 and/or the broach 902 may be displayed on display along with the insertion path 802 to enable the surgeon to visually identify and follow the insertion path 802.

In another embodiment, broach 902 may be removably coupled to a hand tool (not shown) separate from end effector 20. The surgeon may operate the hand tool to insert broach 902 into femur 602. In such an embodiment, the position of broach 902 and/or the hand tool may be tracked by navigation system (e.g., by localizer 44) and the real-time position data of femur 602 and the hand tool and/or broach 902 may be displayed on display 38 in a similar manner as described above.

During the insertion of broach 902, navigation system 32 and/or manipulator 14 may monitor the position of broach 902 with respect to the portion of the patient's anatomy and may determine whether broach 902 has reached the desired final insertion position. If broach 902 has reached the desired final insertion position, the navigation system 32 for instance, transmits a signal to manipulator controller 60 through navigation controller 62 to terminate the insertion of broach 902. In response to the signal, manipulator 14 may halt the insertion of broach 902 at the final insertion position and/or may notify the surgeon by haptic feedback or by another suitable indicator such as an audio or visual signal.

Alternatively, the surgeon may indicate whether broach 902 has reached the desired final insertion position and may notify manipulator controller 60 and/or navigation controller 62 that the final position has been reached. In such an embodiment, localizer 44 and/or manipulator 14 identifies the final position of broach 902 and stores data representative of the final position for later use in inserting the stem and/or injecting the cement.

In one embodiment, localizer 44 continually monitors the position of the portion of the patient's anatomy (e.g., femur 602) and transmits signals representative of the position to manipulator controller 60 via navigation controller 62. In response, manipulator controller 60 may automatically adjust the position of end effector 20 (and thus the position of broach 902) to match any movement of the patient's anatomy. As a result, even if the patient moves while broach 902 is being inserted or after broach 902 has been inserted, manipulator controller 60 may adjust the insertion path 802 and the orientation of end effector 20 to move end effector 20 and/or broach 902 in synchrony with the portion of the patient's anatomy to prevent unintended damage to the portion of the anatomy or deviation from insertion path 802.

Figure 10:
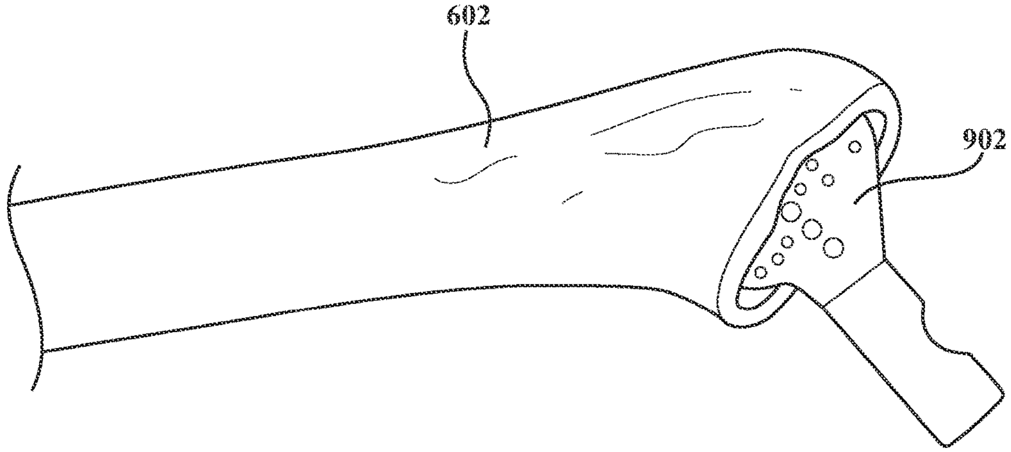
FIG. 10 is a perspective view of a portion of a patient's anatomy to illustrate a final broach position shown in FIG. 4.

FIG. 10 is a perspective view of a portion of a patient's anatomy to illustrate a final broach position that may be used with method 400 (shown in FIG. 4).

As discussed above, localizer 44 tracks the position of broach 902 as broach 902 is inserted into the portion of the patient's anatomy (e.g., the femur 602). When navigation controller 62 and/or manipulator controller 60 determines that broach 902 has reached the final broach position (also referred to as the final insertion position), the final broach or insertion position is captured by navigation system 32 and/or manipulator computer 26 based on the determined position of broach 902 and/or end effector 20 as well as the position of the portion of the patient's anatomy. The final insertion position may be used to determine the location for the implant to be inserted to (hereinafter referred to as the final implant position). Alternatively, the final implant position may be determined based on the position of the implant identified during the planning phase or with intraoperative modification of the plan identified in the planning phase.

Figure 11:
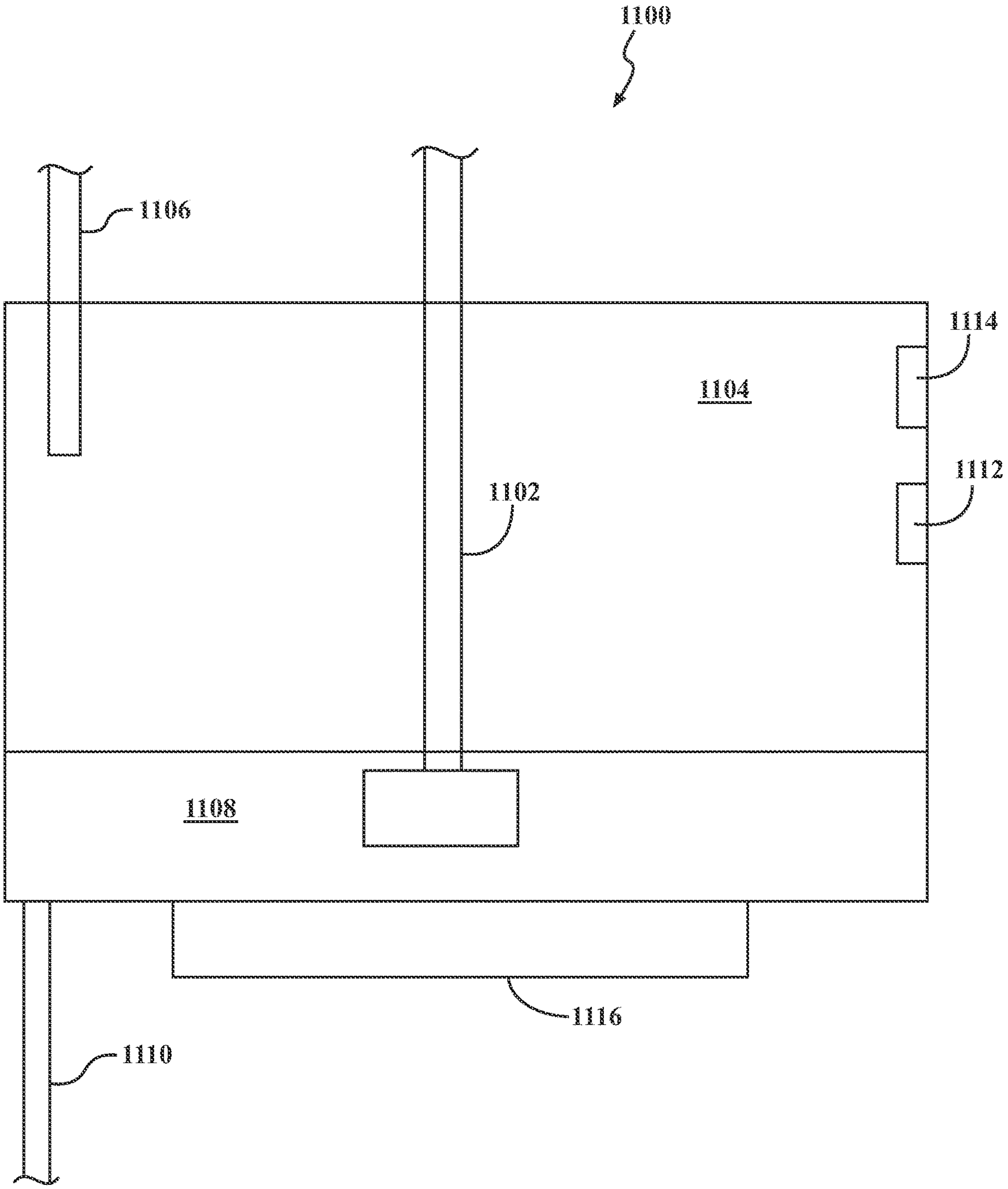
FIG. 11 is a side view of an exemplary cement mixing apparatus that may be used with the preparing and monitoring cement step shown in FIG. 4.

FIG. 11 is a side view of an exemplary cement mixing apparatus 1100 that may be used with the preparing and monitoring cement step 412 of method 400 (shown in FIG. 4).

As described herein, a predetermined amount of bone cement is prepared and injected into the cavity 903 formed in the portion of the patient's anatomy (e.g., the femur 602). In one embodiment, the bone cement is the Simplex® brand bone cement manufactured by Stryker Corporation. Alternatively, any other suitable bone cement or adhesive may be used. The adhesive may be administered as two or more pastes, powders, or other constituent parts that may be mixed together in a nozzle or other portion of the cement mixing apparatus 1100 or that may be mixed together at the cavity 903.

In one embodiment, cement mixing apparatus 1100 includes a cement mixer 1102 that is disposed in or insertable into a mixing chamber 1104. A liquid inlet 1106 introduces a predetermined amount of liquid monomer into mixing chamber 1104 which mixes with a predetermined amount of cement powder 1108 to yield a desired amount of bone cement. A cement outlet 1110 may be used to provide the mixed bone cement to a cement injector (not shown in FIG. 11) which in turn may be used to inject the cement into the cavity.

In one embodiment, cement mixing apparatus 1100 may be similar to the apparatus described in U.S. Pat. No. 8,657,482, the disclosure of which is hereby incorporated herein in its entirety. The cement mixing apparatus 1100 may thus be a separate apparatus that mixes the cement apart from manipulator 14. Alternatively, cement mixing apparatus 1100 may be attached to or included within an end effector 20 or other portion of manipulator 14. For example, cement mixing apparatus 1100 may be removably coupled to end effector 20 in a similar manner as the broach described above. Still alternatively, cement may be manually mixed by the surgeon or another health care professional in a separate mixing chamber.

In an embodiment in which cement mixing apparatus 1100 is coupled to, or is a part of, end effector 20 or another suitable portion of manipulator 14, a temperature of the mixed cement and/or mixing chamber 1104 may be monitored by a temperature sensor 1112 in communication with manipulator controller 60. A humidity of air within mixing chamber 1104 (or the ambient air) may be measured by a humidity sensor 1114 in communication with manipulator controller 60.

During the mixing of the cement, manipulator controller 60 may control mixer 1102 to mix the liquid monomer and cement powder at a predetermined rotation speed for a first predetermined amount of time (hereinafter referred to as the "cement mixing time") based on the measured temperature and humidity. After the cement has been mixed for the cement mixing time, mixer 1102 is stopped and removed from the mixing chamber 1104. Manipulator controller 60 then waits until a second predetermined amount of time (hereinafter referred to as the "cement setting time") has elapsed to help ensure that the cement reaches a suitable viscosity for injection into the cavity.

In one embodiment, cement mixing apparatus 1100 includes a temperature control element 1116 (e.g., a heating coil or element and/or a cooling coil or element) that may be controlled by manipulator controller 60 to maintain a desired temperature of mixing chamber 1104. In such an embodiment, a consistency of the mixed cement may be increased.

Figure 12:
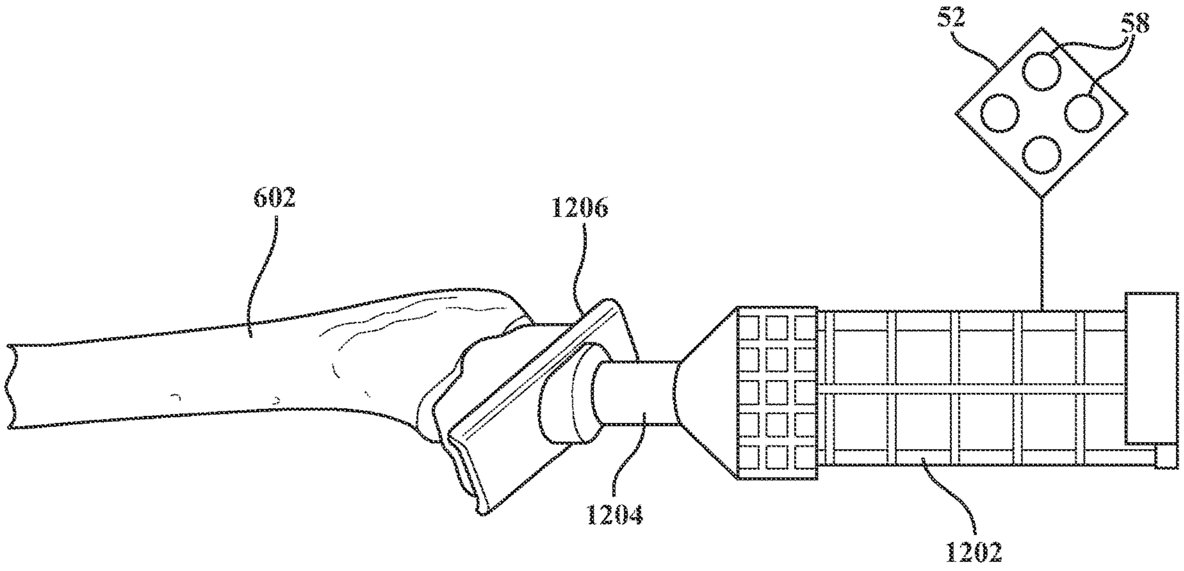
FIG. 12 is a side view of an exemplary cement injector that may be used with the cement injecting and pressurizing step shown in FIG. 4.

FIG. 12 is a side view of an exemplary cement injector 1202 that may be used with the cement injecting and pressurizing step 414 of method 400 (shown in FIG. 4).

Cement may be injected into cavity 903 using cement injector 1202 after broach 902 is removed and after the cement setting time has elapsed. In one embodiment, cement injector 1202 is a part of, or is removably coupled to, end effector 20 such that manipulator 14 may operate cement injector 1202 to automatically inject the cement into the cavity at a pressure and a rate controlled and monitored by manipulator controller 60. For example, cement injector 1202 may be removably coupled to end effector 20 in a similar manner as the broach described above. Alternatively, cement injector 1202 may be included within cement mixing apparatus 1100. In another embodiment, cement injector 1202 may be a hand tool that is manually operated by a surgeon to inject the cement into the cavity.

In an embodiment in which cement injector 1202 is automatically controlled by manipulator controller 60, a motor (not shown) coupled to or included within cement injector 1202 may be controlled by manipulator controller 60 to inject a predetermined amount or volume of cement into the cavity at a first predetermined pressure ("cement injection pressure"). A pressure sensor coupled to or included within cement injector 1202 may be used to monitor the pressure of the cement injection and may transmit signals to manipulator controller 60 representative of the pressure. The cement injection pressure may be consistently monitored and maintained by manipulator controller 60 to backfill the cement in the cavity 903 while avoiding or minimizing the formation of air pockets in the cement and cavity 903.

In one embodiment, a nozzle 1204 of cement injector 1202 may be formed of a suitably stiff material that enables nozzle 1204 to be accurately tracked by localizer 44 based on tracking of the cement injector 1202 via a tracker 52 attached to the cement injector 1202 and/or encoder data from the manipulator 14. A known relationship between the tracker 52 and the nozzle 1204 may be separately stored in the controller 30 for access by the navigation controller 62 to determine a position and/or orientation of the nozzle 1204 or opening therein. In such a manner, localizer 44 may transmit signals representative of the current position and orientation of nozzle 1204 and cement injector 1202 to manipulator controller 60 (through navigation controller 62) to enable manipulator controller 60 to controllably backfill cement into the cavity 903.

Once the cement has been injected, a plug 1206 may be placed over the opening of the cavity 903 to pressurize the injected cement at a second predetermined pressure ("cement hold pressure"). Plug 1206 may be a part of cement injector 1202, or plug 1206 may be separate from injector 1202. In an embodiment, end effector 20 may use cement injector 1202 to hold plug 1206 in place with the cement hold pressure for a third predetermined amount of time (hereinafter referred to as "cement pressurization time") to ensure that the cement has adhered properly to the surrounding bone or other portion of the patient's anatomy. In another embodiment, a cement pressurizer tool (e.g., a proximal cement pressurizer) may be removably attached to end effector 20 to hold plug 1206 in place for the cement pressurization time.

Alternatively, a surgeon or other health care professional may inject the cement and/or may hold plug 1206 in place for the cement pressurization time. In such an embodiment, manipulator controller 60 may monitor the pressure of plug 1206 and may display the pressure on display 38 to enable the surgeon or other health care professional to adjust the pressure at which plug 1206 is held in place to achieve the desired cement hold pressure.

After the cement pressurization time has elapsed, plug 1206 is removed and the implant is prepared for insertion.

Figure 13:
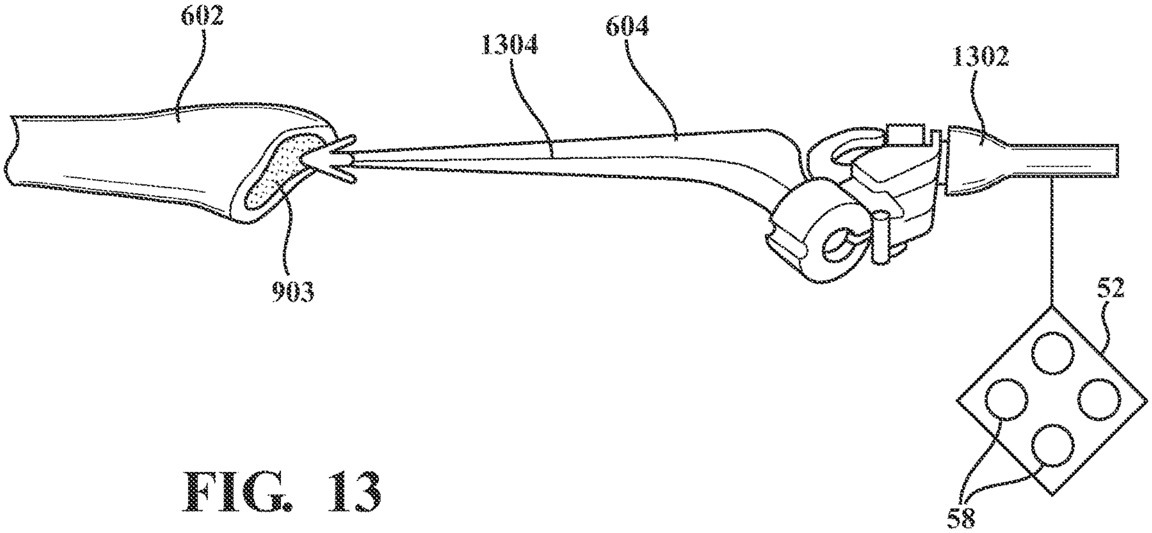
FIG. 13 is a side view of a portion of a patient's anatomy and a stem insertion tool that may be used with the robotically aligning and inserting a femoral stem step shown in FIG. 4.

FIG. 13 is a side view of a portion of a patient's anatomy and a stem insertion tool 1302 that may be used to robotically align and insert the stem 604 to the final broach position, as in step 416 of method 400 (shown in FIG. 4).

In one embodiment, end effector 20 may include stem insertion tool 1302, or stem insertion tool 1302 may be removably coupled to end effector 20. Stem 604 may be removably attached to insertion tool 1302 in preparation for either an automatic or manual insertion into cavity 903. The stem insertion tool 1302 may also include a separate tracker 52 useful for tracking a position and/or orientation of the stem insertion tool 1302 and stem attached thereto in the same manner as the broaches are tracked as previously described. In one embodiment, stem 604 may be removably coupled to end effector 20 and/or stem insertion tool 1302 in a similar manner as the broach described above. Likewise, stem insertion tool 1302 may be removably coupled to end effector 20 in a similar manner.

In an embodiment in which stem 604 is automatically inserted into the cavity 903 by manipulator 14, manipulator controller 60 automatically aligns the stem 604 with the insertion path 802 based on position data received from localizer 44 and navigation controller 62. More specifically, a longitudinal axis 1304 of stem 604 is aligned with insertion path 802 using position and orientation signals received from localizer 44 and navigation controller 62. Manipulator controller 60 causes end effector 20 to insert stem 604 into cavity 903 such that stem 604 moves along insertion path 802 into and through the cavity 903. Alternatively, a customized insertion path 802 may be defined by a surgeon that takes into account the specific anatomy of the patient, such as the anatomy of the proximal femur. For example, the stem 604 may need to be inserted in an initially varus orientation until the shoulder of the stem 604 has moved into the greater trochanter. Afterward, the implant path 802 can correct the orientation of the stem 604 to align with a desired axis of the final implant position as the stem 604 is advanced to the final implant position. Navigation system 32 and/or the manipulator 14 monitors the position of stem 604 using localizer 44 and/or encoder data and notifies manipulator controller 60 when stem 604 has reached the final implant position. As discussed above, the final implant position may be the final broach position determined above, or may be the planned implant position determined during the planning or intra-operative trialing phases. When manipulator controller 60 receives the notification that stem 604 has reached the final implant position, manipulator 14 terminates the movement of stem 604 and holds stem 604 in the final implant position.

Alternatively, in the example of manual insertion of stem 604 into the cavity 903 by a surgeon where stem 604 is coupled to end effector 20, the surgeon aligns stem 604 with the insertion path. The orientation and position of stem 604 may be monitored by navigation system 32 and may be displayed on display 38 along with insertion path 802. Manipulator controller 60 and/or navigation controller 62 may notify the surgeon if the orientation of stem 604 deviates from the insertion path 802 by a predetermined amount. Manipulator controller 60 and/or navigation controller 62 may cause the notification to be displayed on display 38 as an alert and/or may cause end effector 20 to notify the surgeon via haptic feedback. In addition, manipulator controller 60 may prevent the surgeon from deviating from the insertion path 802 by preventing the surgeon from moving stem 604 (and thereby end effector 20) past a boundary set by boundary generator 66. Additionally or alternatively, navigation system 32 may display insertion path 802 and the current position of stem 604 on display 38 to enable the surgeon to visually determine whether stem 604 is aligned with insertion path 802 and/or whether the insertion of stem 604 has deviated from insertion path 802.

In one embodiment, localizer 44 continually monitors the position of the portion of the patient's anatomy (e.g., femur 602 in this embodiment) and transmits signals representative of the position to manipulator controller 60 via navigation controller 62. In response, manipulator controller 60 may automatically adjust the position of end effector 20 (and thus the position of stem 604) to match any movement of the patient's anatomy. As a result, even if the patient moves while stem 604 is being inserted or after the stem 604 has been inserted, manipulator controller 60 may adjust insertion path 802 and the orientation of end effector 20 to move end effector 20 and/or stem 604 in synchrony with the portion of the patient's anatomy to prevent unintended damage to the portion of the anatomy or deviation from the insertion path 802.

Manipulator controller 60 and/or navigation controller 62 may determine the insertion speed of the stem 604 based on position data received from localizer 44 and/or encoder data. Manipulator controller 60 may control the speed at which stem 604 is inserted to reduce the amount of cement voids created by the insertion. If the surgeon manually inserts the stem 604, manipulator controller 60 or navigation controller 62 may display the insertion speed on display 38 as well as any warnings or alerts if the speed exceeds a desired insertion speed or another suitable speed threshold. Alternatively, the surgeon may control the insertion speed based on the polymerization state of the cement, or based on any other suitable factors.

In one embodiment, manipulator controller 60 inserts stem 604 along insertion path 802 to achieve a desired thickness of cement surrounding stem 604 or to otherwise ensure that a complete mantel of cement will surround stem 604. More specifically, stem 604 is inserted along insertion path 802 such that each circumferential location along an outer surface of stem 604 is a predetermined distance from an opposing inner surface of the femoral bone defining cavity 903. In such a manner, the stem 604 is anchored to the surrounding bone in a more efficient and robust manner.

Figure 14:
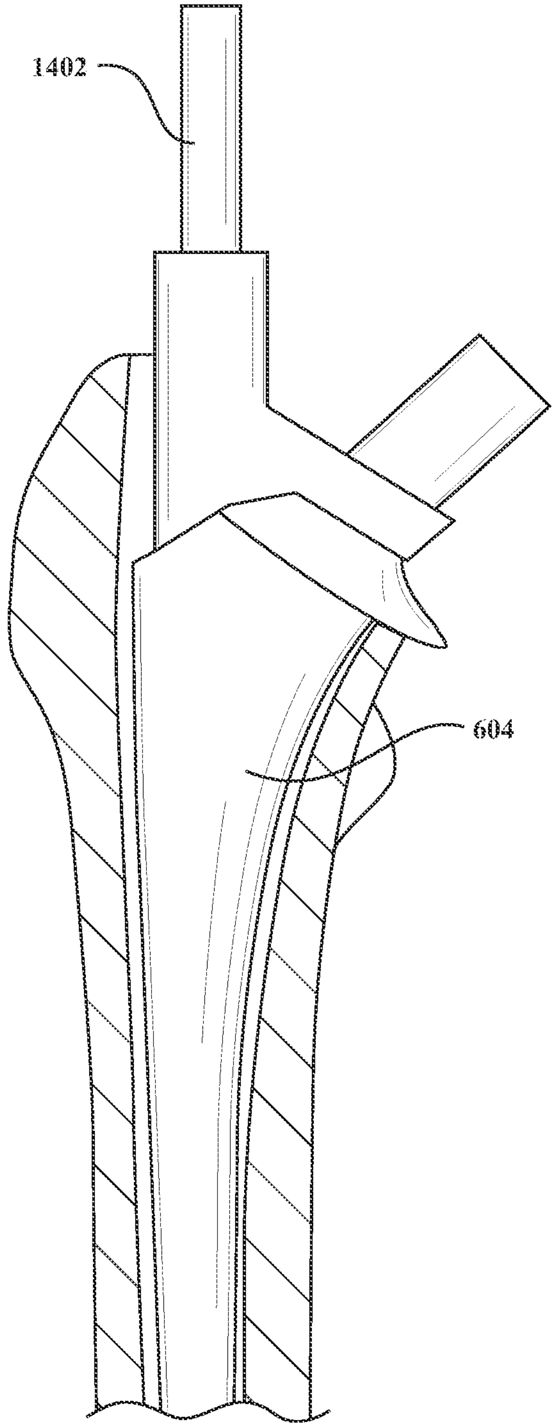
FIG. 14 is a perspective view of an exemplary positioning tool that may be used with the step of maintaining the stem in the final implant position shown in FIG. 4.

FIG. 14 is a perspective view of an exemplary positioning tool 1402 that may be used with the step of maintaining 418 the stem in the final implant position of method 400 (shown in FIG. 4).

When navigation system 32 determines that stem 604 has reached the final insertion position, navigation system 32 transmits a signal to manipulator controller 60 via navigation controller 62 indicating the same. When manipulator controller 60 receives the signal, manipulator controller 60 stops inserting stem 604 and maintains stem 604 in the final implant position such that stem 604 is prevented from moving axially or transversely within cavity. The stem 604 may be automatically maintained in the final implant position relative to the femur even if the patient moves by causing the stem 604 to automatically match the movement of the femur (i.e., by automatically moving end effector 20 to which the stem 604 is attached), as described more fully herein. Alternatively, the stem 604 may be released after it has been placed in the final implant position, and the surgeon may manually maintain the stem 604 in position until the cement has cured or polymerized.

In one embodiment, positioning tool 1402 is the implant insertion tool 1302. Alternatively, a separate positioning tool 1402 may be attached to or otherwise provided on end effector 20. In one embodiment, positioning tool 1402 may be removably coupled to end effector 20 in a similar manner as the broach described above. Manipulator 14 may press and engage positioning tool 1402 of end effector 20 against a portion of stem 604 to maintain stem 604 in place within the cavity 903 of the portion of the patient's anatomy (e.g., the femur 602). Alternatively, manipulator controller 60 may cause end effector 20 to lock in place such that end effector 20 (and positioning tool 1402) are prevented from moving, thus maintaining the stem 604 in the final implant position. Still alternatively, end effector 20 may attach a flange or other portion of end effector 20 to a portion of the patient's anatomy (such as bone) to prevent movement of the patient's anatomy relative to the end effector 20.

As described above, in one embodiment, localizer 44 continually monitors the position of the portion of the patient's anatomy and transmits signals representative of the position to manipulator controller 60 via navigation controller 62. In response, manipulator controller 60 may automatically adjust the position of end effector 20 to match any movement of the patient's anatomy. As a result, if the patient moves while stem 604 is maintained in the final implant position, manipulator controller 60 may adjust the orientation of end effector 20 to move end effector 20 and stem 604 in synchrony with the portion of the patient's anatomy. Alternatively, navigation system 32 may determine what movement of end effector 20 is required to match the patient's movement and may transmit signals representative of the required movement to manipulator controller 60. In response to the signals received from navigation system 32, manipulator controller 60 may control end effector 20 to move responsively to match the movement of the patient's anatomy.

Manipulator controller 60 monitors an amount of time in which stem 604 is held in the final insertion position. A fourth predetermined amount of time (hereinafter referred to as the "stem hold time") that is needed for the cement within cavity 903 to cure or polymerize is identified by manipulator controller 60. Manipulator controller 60 controls end effector 20 to hold stem 604 in the final insertion position until the stem hold time has elapsed. Once manipulator controller 60 determines that the cement has cured (e.g., the stem hold time has elapsed), stem 604 is disconnected from end effector 20 and/or positioning tool 1402. Alternatively, the stem 604 may be disconnected from the end effector 20 and/or positioning tool 1402 before the stem hold time elapses. For example, the stem 604 may be disconnected from the end effector 20 and/or positioning tool 1402 after the stem 604 has been placed in the final implant position and the surgeon may ensure that the stem 604 maintains its position until the cement has cured or polymerized.

In one embodiment, manipulator controller 60 automatically releases stem 604 from end effector 20 after the stem hold time has elapsed. Alternatively, a surgeon or other health care professional may manually release stem 604 from end effector 20 when the stem hold time has elapsed.

Figure 15:
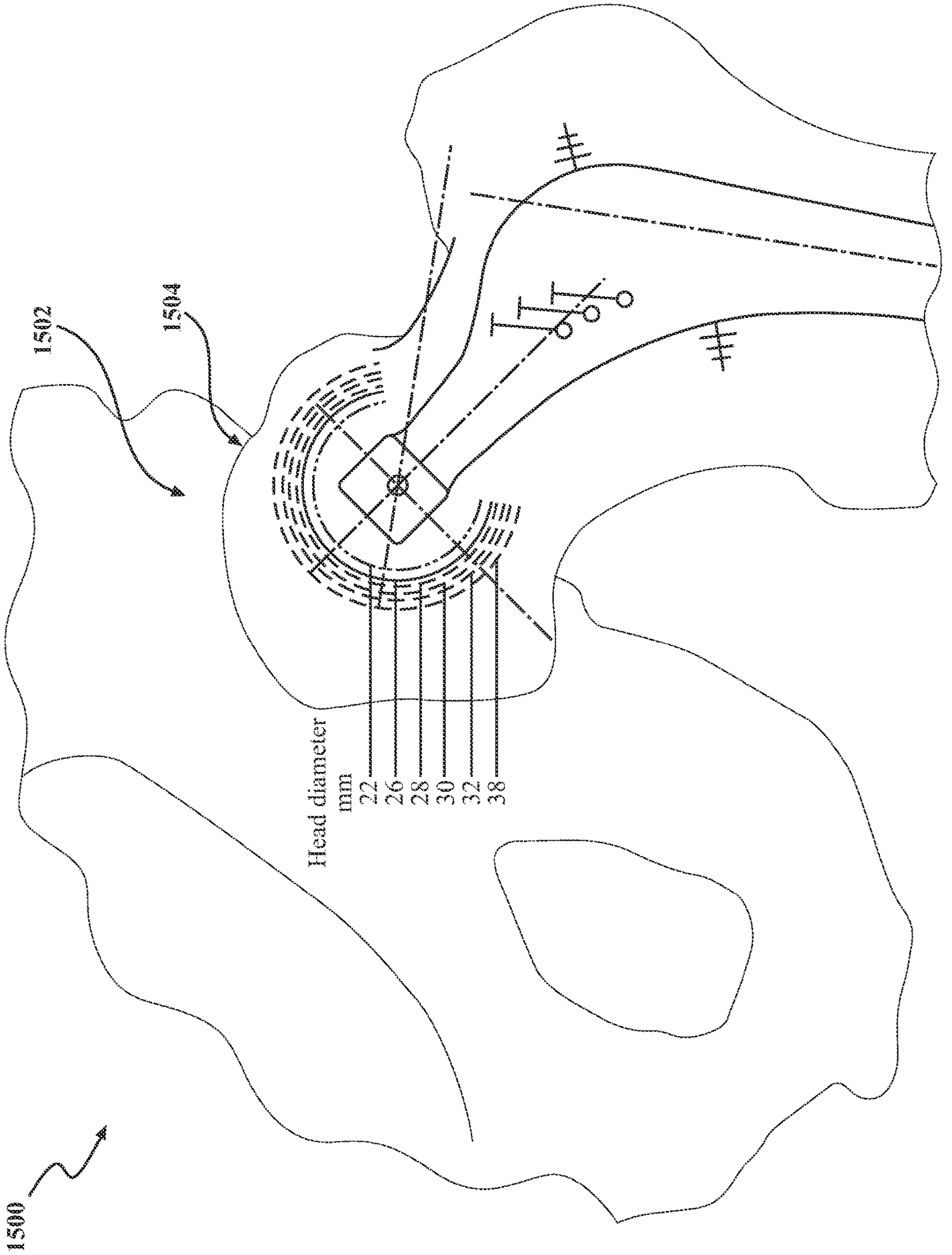
FIG. 15 is another image of a portion of a patient's anatomy into which an implant is planned to be inserted.

FIG. 15 is an image of a portion of a patient's anatomy into which an implant is planned to be inserted. Specifically, FIG. 15 illustrates an x-ray image 1500 of a portion of a patient's acetabulum 1502 and an outline of an acetabular cup 1504 that is planned to be inserted into acetabulum 1502. FIG. 15 illustrates part of planning an insertion of an acetabular cup into a portion of a patient's anatomy and the planning of cement holes referenced by step 502 of method 500 (shown in FIG. 5). While FIG. 15 is described with reference to x-ray images, it should be recognized that other imaging modalities may be used instead, such as MRI, CT scan, ultrasound, etc. In addition, the images may be two-dimensional (2D), three-dimensional (3D), or a combination thereof (e.g., biplanar x-ray imaging).

In one embodiment, the outline of the implant is computer-generated and superimposed on the image of acetabulum 1502 to assist a surgeon in planning the location and dimensions of the implant. The surgeon may select an acetabular cup 1504 having a desired size from a predefined list or catalog of acetabular cup sizes to achieve an optimal fit within the x-ray image and to achieve an optimal fit with the planned femoral stem, for example.

In one embodiment, navigation system 32 displays the x-ray image (or other cross-sectional image) on display 38 and displays the computer-generated image of the selected acetabular cup implant on the x-ray image on display 38. The surgeon determines the appropriate size of the acetabular cup 1504 that will enable a desired amount of bone surrounding the acetabular cup 1504 to provide a suitable and stable support for the implant. The size and placement of the planned acetabular cup takes into account a planned thickness of cement that is to be injected into a cavity defined in the acetabulum 1502 to secure the acetabular cup 1504 in the cavity.

The surgeon also plans the alignment of the cavity to receive acetabular cup 1504 such that a central axis of the planned cavity has a predefined angle with respect to a surface of the portion of the patient's anatomy, such as the acetabulum 1502. The surgeon also plans the number, location, width, depth, and axial angles of cement holes to be formed in the cavity for receiving bone cement during the surgical procedure. Alternatively, navigation system 32 or another suitable system plans the alignment of the planned cavity and the number, location, width, depth, and angles of the cement holes.

Once the surgeon has selected the final implant size, position, and alignment of the implant and cement holes, navigation system 32 translates the position and orientation of the planned acetabular cup 1504 position and cement holes into the localizer coordinate system LCLZ in preparation for determining the planned insertion path of the acetabular cup implant and the planned cement holes for the bone cement.

Figure 16:
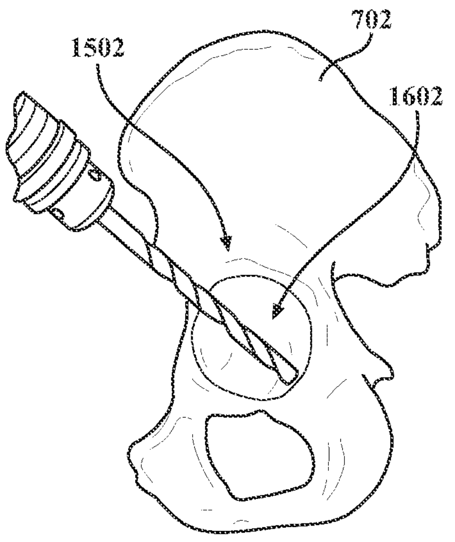
FIG. 16 is a perspective view of a portion of a patient's anatomy that may be used to illustrate the preparation of the anatomy step shown in FIG. 5.

FIG. 16 is a perspective view of a portion of a patient's pelvis 702 and the acetabulum 1502 included therein that may be used to illustrate the preparation of the acetabulum 1502 as set forth in step 504 of method 500 (shown in FIG. 5).

During the acetabular preparation step, osteophytes and cancellous bone are removed to form a cavity 1602 in acetabulum 1502. Cavity 1602 is formed in acetabulum 1502 with a central axis having a predefined angle with respect to a surface of the acetabulum 1502 such that central axis is coaxial with respect to a central axis of a head of a stem that is planned to be inserted into the femur. In addition, cavity 1602 is planned to have suitable dimensions to receive an acetabular cup 1504 sized to match a planned femoral stem and to also include a mantle of bone cement having a predetermined thickness surrounding the planned acetabular cup 1504.

The axial angle, position, and dimensions of cavity 1602 and acetabular cup 1504 to be inserted therein may be calculated during the planning step 502 of method 500 and may be stored in a memory of navigation computer 36 or another suitable storage device. During the surgical procedure to form cavity 1602, navigation controller 62 or another suitable controller may reference the planned axial angle, dimensions, and position of cavity 1602 and translate the angle, dimensions, and position to the manipulator coordinate system MNPL.

Once the axial angle, dimensions, and position of cavity 1602 has been translated or otherwise determined, manipulator controller 60 may control end effector 20 and energy applicator 24 to automatically ream or otherwise remove the osteophytes and bone of acetabulum 1502 to form cavity 1602. For example, in one embodiment, a bur may be used to remove the osteophytes and cancellous bone of acetabulum 1502 to form cavity 1602. Localizer 44 and/or manipulator 14 may continually track the position of the patient's acetabulum 1502, end effector 20, and/or energy applicator 24. Localizer 44 may transmit real-time position data to manipulator controller 60 through navigation controller 62. Manipulator controller 60 may use the real-time position data, encoder data, and data representing the axial angle and position of cavity 1602 to ensure that energy applicator 24 does not deviate from the planned cavity axial angle, dimensions, and position.

More specifically, in one embodiment, path generator 69 may create a movement path for energy applicator 24 that corresponds to the planned axial angle and position. Alternatively, path generator 69 may create a movement path that may not correspond to the planned axial angle but that is still operative to form cavity 1602 with the desired dimensions, position, and axial angle. Navigation controller 62 and/or manipulator controller 60 may track the position of end effector 20 via signals received from localizer 44 and/or encoder data. Navigation controller 62 may transmit the position data to manipulator controller 60. Manipulator controller 60 may automatically guide energy applicator 24 along the movement path based on the position data and/or encoder data while energy applicator 24 is operating (e.g., reaming, burring, or drilling) to cause energy applicator 24 to remove the cancellous bone and osteophytes in acetabulum 1502 to form cavity 1602.

Alternatively, cavity 1602 may be formed by a surgeon operating a hand tool such as a saw, bur, reamer, or drill, or by the surgeon operating end effector 20 and energy applicator 24 in a manual mode. The manual mode may include a haptics-based mode in which manipulator controller 60 prevents the surgeon from removing bone outside of the planned cavity position and dimensions, or in which manipulator controller 60 generates a haptics-based alert, such as a vibration, to the surgeon if the surgeon deviates from the planned cavity position and dimensions. Alternatively or additionally, the manual mode may include a navigated mode in which the progress of the cavity formation (i.e., the removal of the cancellous bone and osteophytes) is displayed on display 38 so that the surgeon can visually identify how the cavity formation tracks the planned cavity dimensions and position. In each of the haptics-based and navigated modes, the position of the portion of the patient's anatomy that the surgeon is operating on (i.e., the acetabulum 1502 in this case) and the position of the end effector 20 and/or energy applicator 24 may be tracked in real-time by localizer 44 and/or manipulator 14 and may be displayed on display 38 and/or may be communicated to manipulator controller 60 via navigation controller 62.

Figure 17:
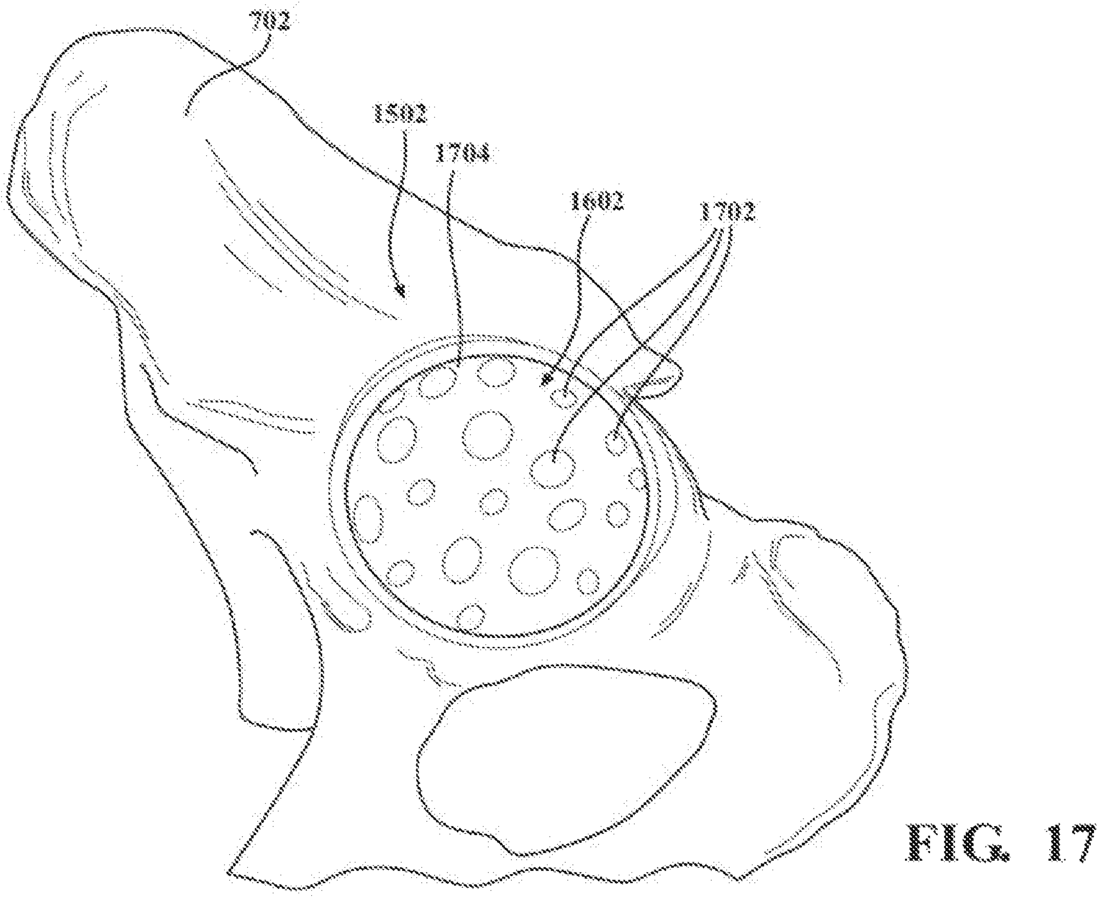
FIG. 17 is a perspective view of a portion of a patient's anatomy that may be used to illustrate the formation of cement holes in an acetabular cavity step shown in FIG. 5.

FIG. 17 is a perspective view of a portion of a patient's pelvis 702 and the acetabulum 1502 included therein that may be used to illustrate the formation of cement holes 1702 in an acetabular cavity 1602 as set forth in step 506 of method 500 (shown in FIG. 5).

During the cement hole formation step, a predetermined number of cement holes 1702 are drilled or otherwise created in a wall 1704 of the acetabulum accessed via the cavity 1602. Each hole 1702 has a predetermined depth, and the depth of each hole 1702 may be the same or different than a depth of each other hole 1702. Each hole 1702 is formed with an axis having a predetermined angle with respect to the axis of the cavity 1602. In one embodiment, the cement holes 1702 are formed with the number, location, axial angle, depth, and width (hereinafter referred to as the cement hole characteristics) set forth in the planning stage 502. More specifically, the cement hole characteristics may be calculated during the planning step 502 of method 500 and may be stored in a memory of navigation computer 36 or another suitable storage device.

During the surgical procedure to form cement holes 1702, navigation controller 62 or another suitable controller may reference the cement hole characteristics and translate the cement hole characteristics to the manipulator coordinate system MNPL. Manipulator 14 may operate end effector 20 and energy applicator 24 to automatically drill or otherwise form cement holes 1702 in wall 1704 of cavity 1602. Localizer 44 and/or the manipulator 14 may continually track the position of the patient's acetabulum 1502, end effector 20, and/or energy applicator 24. Localizer 44 may transmit real-time position data to manipulator controller 60 through navigation controller 62. Manipulator controller 60 may use the real-time position data, encoder data, and data representing the axial angle and position of cavity 1602, end effector 20, and/or energy applicator to ensure that energy applicator 24 forms cement holes 1702 with the planned cement hole characteristics.

More specifically, in one embodiment, path generator 69 may create a movement path for energy applicator 24 that corresponds to the cement hole characteristics for each cement hole 1702 (e.g., the location, depth, axial angle, and width). Navigation controller 62 may track the position of end effector 20 via signals received from localizer 44 and may transmit the position data to manipulator controller 60. Manipulator controller 60 may automatically guide energy applicator 24 along the movement path based on the position data and/or encoder data while energy applicator 24 is operating (e.g., drilling or burring) to cause energy applicator 24 to form each cement hole 1702 with the planned cement hole characteristics.

Alternatively, cement holes 1702 may be formed by a surgeon operating a hand tool such as a saw, bur, or drill, or by the surgeon operating end effector 20 and energy applicator 24 in a haptics-based or navigated manual mode in a similar manner as described above with respect to the acetabular cavity preparation stage. In each of the haptics-based and navigated modes, the position of the portion of the patient's anatomy that the surgeon is operating on (i.e., the acetabulum 1502) and the position of the end effector 20 and/or energy applicator 24 may be tracked in real-time by localizer 44 and/or manipulator 14 and may be displayed on display 38 and/or may be communicated to manipulator controller 60 via navigation controller 62.

Figure 18:
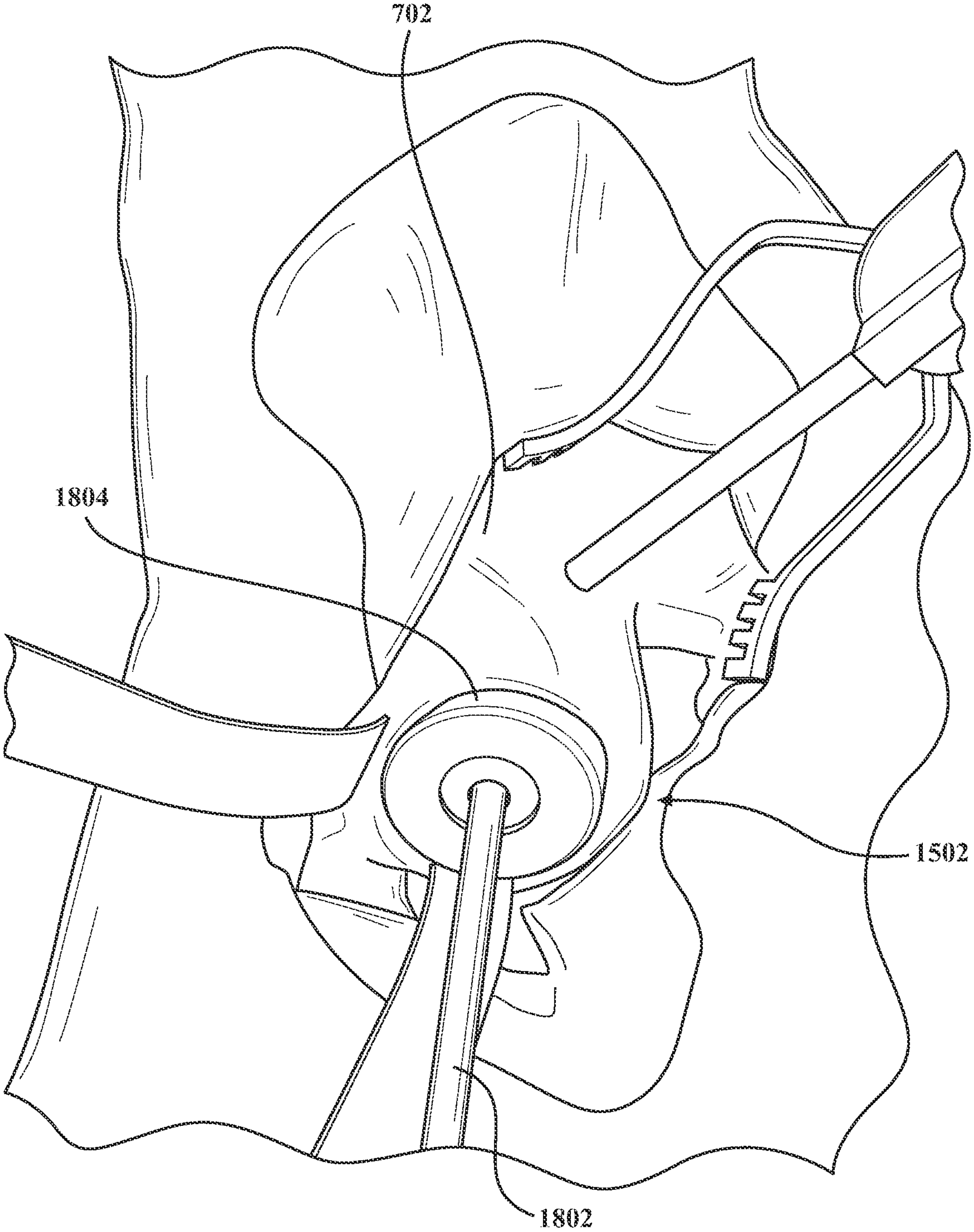
FIG. 18 is a perspective view of an exemplary cement pressurizer tool that may be used with the injecting and pressurizing step shown in FIG. 5.

FIG. 18 is a perspective view of an exemplary cement pressurizer tool 1802 that may be used with the injecting and pressurizing step 510 of method 500 (shown in FIG. 5). In one embodiment, cement pressurizer tool 1802 is an acetabular cement pressurizer.

In an exemplary embodiment, after cement holes 1702 have been formed, a predetermined amount of bone cement or other adhesive may be prepared and injected into cavity 1602 in a similar manner as described above with reference to FIG. 11. In the cement injection phase, cement may be injected into acetabular cavity 1602 and cement holes 1702 using cement injector 1202 after the cement setting time has elapsed. Alternatively, the cement or other adhesive may be injected into acetabular cavity 1602 in the form of one or more pastes, powders, or similar, and the cement (or other adhesive) setting time may commence after the cement or other adhesive is injected. In one embodiment, cement injector 1202 is a part of, or is removably coupled to, end effector 20 such that manipulator 14 may operate cement injector 1202 to automatically inject the cement into cavity 1602 and cement holes 1702 at a pressure and a rate controlled and monitored by manipulator controller 60. Alternatively, cement injector 1202 may be included within cement mixing apparatus 1100. In another embodiment, cement injector 1202 may be a hand tool that is manually operated by a surgeon to inject the cement into cavity 1602 and cement holes 1702. In one embodiment, the cement (or other adhesive) may be injected into the acetabular cavity 1602 through a plug or seal placed over the mouth of the acetabular cavity 1602.

In an embodiment in which cement injector 1202 is automatically controlled by manipulator controller 60, a motor coupled to or included within cement injector 1202 may be controlled by manipulator controller 60 to inject a predetermined amount of cement into cavity 1602 and cement holes 1702 at a first predetermined pressure ("cement injection pressure"). A pressure sensor coupled to or included within cement injector 1202 may be used to monitor the pressure of the cement injection and may transmit signals to manipulator controller 60 representative of the pressure. The cement injection pressure may be consistently monitored and maintained by manipulator controller 60 to backfill the cement in the cavity 1602 and cement holes 1702 while avoiding or minimizing the formation of air pockets in the cement cavity 1602, and cement holes 1702.

In one embodiment, a nozzle 1204 of cement injector 1202 may be formed of a suitably stiff material that enables nozzle 1204 to be accurately tracked by localizer 44 based on tracking of the cement injector 1202 via a tracker attached to the cement injector 1202 and/or encoder data from the manipulator 14. A known relationship between the tracker and the nozzle 1204 may be separately stored in the controller 30 for access by the navigation controller 62 to determine a position and/or orientation of the nozzle 1204 or opening therein. In such a manner, localizer 44 may transmit signals representative of the current position and orientation of nozzle 1204 and cement injector 1202 to manipulator controller 60 (through navigation controller 62) to enable manipulator controller 60 to controllably backfill cement into cavity 1602 and cement holes 1702.

Once the cement has been injected, a plug or seal 1804 may be placed over the opening of the cavity to pressurize the injected cement at a second predetermined pressure ("cement hold pressure"). Alternatively, plug 1804 may be placed over the opening of the cavity first, and the cement or other adhesive may be injected into the cavity through an opening of plug 1804. Plug 1804 may be a part of cement injector 1202, or plug 1804 may be separate from injector 1202. In an embodiment in which plug 1804 is part of cement injector 1202, end effector 20 may hold plug 1804 in place with the cement hold pressure for a third predetermined amount of time (hereinafter referred to as "cement pressurization time") to ensure that the cement has adhered properly to the surrounding bone or other portion of the patient's anatomy. In another embodiment, cement pressurizer tool 1802 may be removably attached to end effector 20 to hold plug 1804 in place for the cement pressurization time.

Alternatively, a surgeon or other health care professional may inject the cement and/or may hold plug 1804 in place for the cement pressurization time. In such an embodiment, manipulator controller 60 may monitor the pressure of plug 1804 and may display the pressure on display 38 to enable the surgeon or other health care professional to adjust the pressure at which plug 1804 is held in place to achieve the desired cement hold pressure.

After the cement pressurization time has elapsed, plug 1804 is removed and the implant (i.e., acetabular cup 1504) is prepared for insertion.

Figure 19:
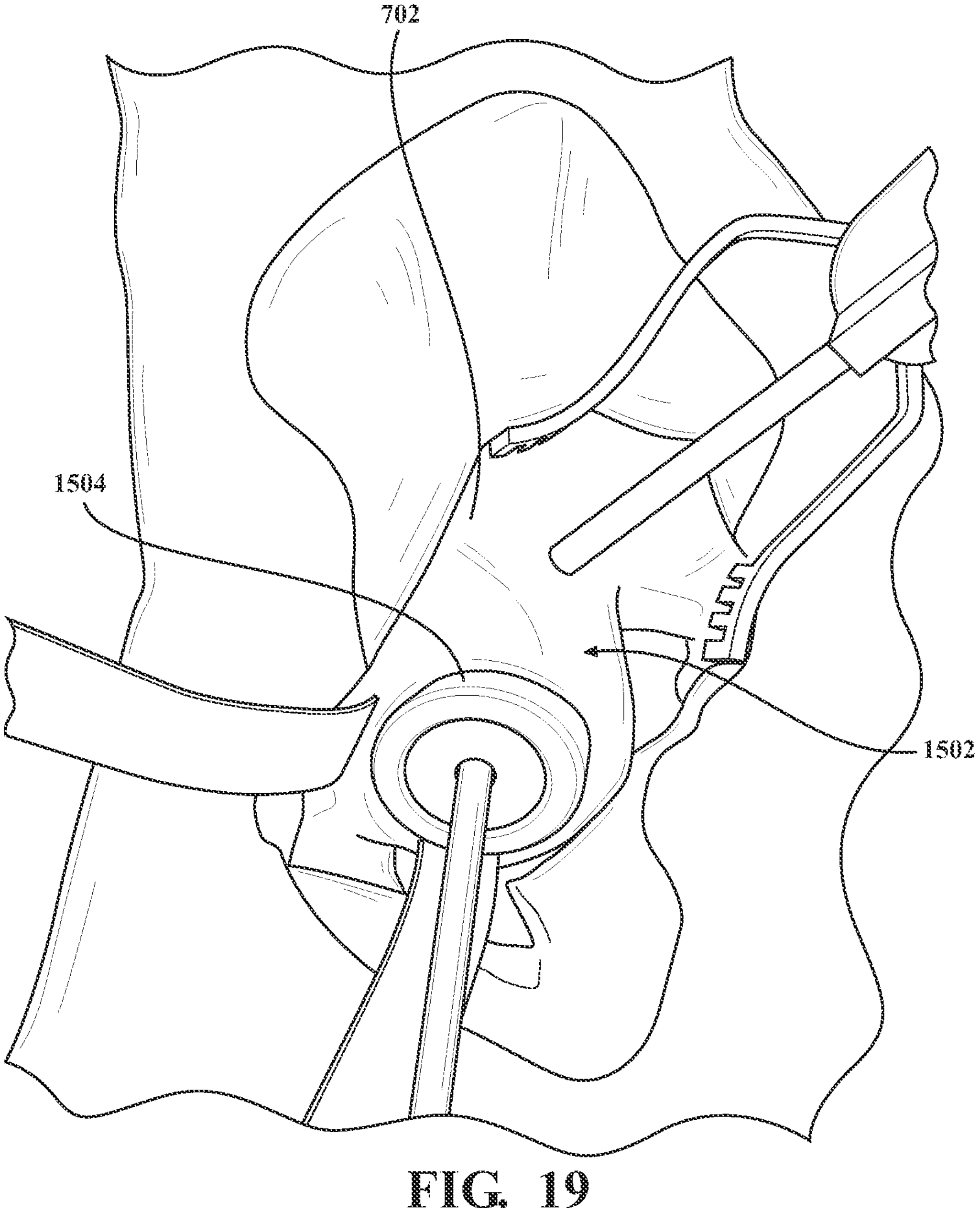
FIG. 19 is a perspective view of a portion of a patient's anatomy and an implant that may be used with the robotically aligning and inserting an acetabular cup step shown in FIG. 5.

FIG. 19 is a view of a portion of a patient's anatomy (i.e., acetabulum 1502) and an implant (acetabular cup 1504) that may be used with the step 512 of method 500 to robotically align and insert the cup to the planned position (shown in FIG. 5).

In one embodiment, end effector 20 may include a cup insertion tool, or the cup insertion tool may be removably coupled to end effector 20 in a similar manner as the broach described above. Acetabular cup 1504 may be removably attached to the insertion tool in preparation for either an automatic or manual insertion into the cavity 1602 in the same manner described above with respect to the stem insertion tool.

In an embodiment in which cup 1504 is automatically inserted into the cavity 1602 by manipulator 14, manipulator controller 60 automatically aligns cup 1504 with an insertion path based on position data received from localizer 44 and navigation controller 62. More specifically, an insertion path is determined that aligns with the center axis of acetabular cavity 1602. A center axis of cup 1504 is aligned with the insertion path using position and orientation signals received from localizer 44 and navigation controller 62. Manipulator controller 60 causes end effector 20 to insert cup 1504 into cavity 1602 such that cup 1504 moves along the insertion path into cavity 1602. Navigation system 32 and/or the manipulator 14 monitors the position and orientation of cup 1504 through localizer 44 and/or encoder data from the manipulator 14. Navigation system 32 may notify manipulator controller 60 via navigation controller 62 when cup 1504 has reached its final implant position (i.e., the position determined in the planning phase). When manipulator controller 60 receives the notification that cup 1504 has reached the final implant position, manipulator 14 terminates the movement of cup 1504 and holds cup 1504 in the final implant position.

Alternatively, in the example of manual insertion of cup 1504 into cavity 1602 by a surgeon where cup 1504 is coupled to end effector 20, the surgeon aligns cup 1504 with the insertion path. The orientation and position of cup 1504 may be monitored by navigation system 32 and may be displayed on display 38 along with insertion path 802. Manipulator controller 60 and/or navigation controller 62 may notify the surgeon if the orientation of cup 1504 deviates from the insertion path by a predetermined amount. Manipulator controller 60 and/or navigation controller 62 may cause the notification to be displayed on display 38 as an alert and/or may cause end effector 20 to notify the surgeon via haptic feedback. In addition, manipulator controller 60 may prevent the surgeon from deviating from the insertion path by preventing the surgeon from moving cup 1504 (and thereby end effector 20) past a boundary set by boundary generator 66. Additionally or alternatively, navigation system 32 may display the insertion path and the current position of cup 1504 on display 38 to enable the surgeon to visually determine whether cup 1504 is aligned with the insertion path and/or whether the insertion of cup 1504 has deviated from the insertion path.

In one embodiment, localizer 44 continually monitors the position of the portion of the patient's anatomy (e.g., acetabulum 1502 or the pelvis in this embodiment) and transmits signals representative of the position to manipulator controller 60 via navigation controller 62. In response, manipulator controller 60 may automatically adjust the position of end effector 20 (and thus the position of cup 1504) to match any movement of the patient's anatomy. As a result, even if the patient moves while cup 1504 is being inserted or after cup 1504 has been inserted, manipulator controller 60 may adjust the insertion path and the orientation of end effector 20 to move end effector 20 and/or cup 1504 in synchrony with the portion of the patient's anatomy to prevent unintended damage to the portion of the anatomy or deviation from the insertion path.

Manipulator controller 60 and/or navigation controller 62 may determine the insertion speed of cup 1504 based on position data received from localizer 44 and/or encoder data from the manipulator 14. Manipulator controller 60 may control the speed at which cup 1504 is inserted to reduce an amount of cement voids created by the insertion. If the surgeon manually inserts cup 1504, manipulator controller 60 or navigation controller 62 may display the insertion speed on display 38 as well as any warnings or alerts if the speed exceeds a desired insertion speed or another suitable speed threshold. Alternatively, the surgeon may control the insertion speed based on the polymerization state of the cement, or based on any other suitable factors.

In one embodiment, manipulator controller 60 inserts cup 1504 along the insertion path to achieve a desired thickness of cement surrounding cup 1504 when cup 1504 is inserted into cavity 1602, or to otherwise ensure that a complete mantel of cement will surround cup 1504 within cavity 1602. More specifically, cup 1504 is inserted along the insertion path such that each location along an outer surface of cup 1504 is a substantially uniform distance from an opposing inner surface of the wall defining cavity 1602. In such a manner, cup 1504 is anchored to the surrounding bone in a more efficient and robust manner. Alternatively, the surgeon may deviate from the insertion path to avoid nearby soft tissue and may realign the cup 1504 with the insertion path as the cup 1504 approaches the final implant position (e.g., when the cup 1504 is within the last 2-5 millimeters of the final implant position, or within another suitable distance).

Figure 20:
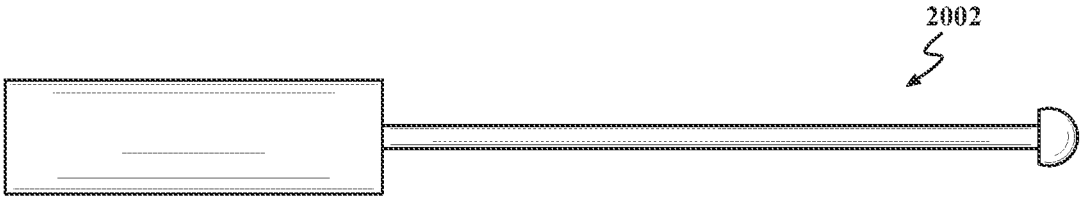
FIG. 20 is a perspective view of an exemplary positioning tool that may be used with the step of maintaining the acetabular cup in the final implant position shown in FIG. 5.

FIG. 20 is a perspective view of an exemplary positioning tool 2002 that may be used with the step 514 of maintaining the cup in the final implant position of method 500 (shown in FIG. 5).

When navigation system 32 determines that cup 1504 has reached the final implant position, navigation system 32 transmits a signal to manipulator controller 60 via navigation controller 62 indicating the same. When manipulator controller 60 receives the signal, manipulator controller 60 stops inserting cup 1504 and maintains cup 1504 in the final implant position such that cup 1504 is prevented from moving axially or transversely within cavity.

In one embodiment, positioning tool 2002 is the same tool as the implant insertion tool. Alternatively, a separate positioning tool 2002 may be attached to or otherwise provided on end effector 20. Manipulator 14 may press positioning tool 2002 of end effector 20 against cup 1504 with a predetermined pressure to hold cup 1504 in place within the cavity 1602 of the portion of the patient's anatomy (e.g., the acetabulum 1502). Alternatively, manipulator controller 60 may cause end effector 20 to lock in place such that end effector 20 (and positioning tool 2002) are prevented from moving, thus maintaining the cup 1504 in the final implant position. Still alternatively, end effector 20 may attach a flange or other portion of end effector 20 to a portion of the patient's anatomy (such as a portion of the pelvic bone adjacent to the acetabulum 1502) to prevent movement of the patient's anatomy relative to end effector 20.

As described above, in one embodiment, localizer 44 continually monitors the position of the portion of the patient's anatomy and transmits signals representative of the position to manipulator controller 60 via navigation controller 62. In response, manipulator controller 60 may automatically adjust the position of end effector 20 to match any movement of the patient's anatomy. As a result, if the patient moves while cup 1504 is maintained in the final implant position, manipulator controller 60 may adjust the orientation of end effector 20 to move end effector 20 and/or cup 1504 in synchrony with the portion of the patient's anatomy. Alternatively, navigation system 32 may determine what movement of end effector 20 is required to match the patient's movement and may transmit signals representative of the required movement to manipulator controller 60. In response to the signals received from navigation system 32, manipulator controller 60 may control end effector 20 to move responsively to match the movement of the patient's anatomy.

Manipulator controller 60 monitors an amount of time in which cup 1504 is held in the final implant position. A predetermined amount of time (hereinafter referred to as the "cup hold time") that is needed for the cement within cavity 1602 to cure or polymerize is identified by manipulator controller 60. Manipulator controller 60 controls end effector 20 to hold cup 1504 in the final implant position until controller 60 determines that the cement has cured (e.g., the cup hold time has elapsed). Once the cup hold time has elapsed, cup 1504 is disconnected from end effector 20 and/or positioning tool 2002. Alternatively, cup 1504 may be disconnected from end effector 20 and/or positioning tool 2002 before the cup hold time elapses. For example, cup 1504 may be disconnected from end effector 20 and/or positioning tool 2002 after cup 1504 has been placed in the final implant position and the surgeon may ensure that cup 1504 maintains its position until the cement has cured or polymerized.

In one embodiment, manipulator controller 60 automatically releases cup 1504 from end effector 20 after the cup hold time has elapsed. Alternatively, a surgeon or other health care professional may manually release cup 1504 from end effector 20 when the cup hold time has elapsed.

Although specific features of various embodiments of the disclosure may be shown in some drawings and not in others, this is for convenience only. In accordance with the principles of the disclosure, any feature of a drawing or other embodiment may be referenced and/or claimed in combination with any feature of any other drawing or embodiment.

This written description uses examples to describe embodiments of the disclosure and also to enable any person skilled in the art to practice the embodiments, including making and using any devices or systems and performing any incorporated methods. The patentable scope of the disclosure is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

What is claimed is:

1. A surgical system to facilitate insertion of a stem implant into a cavity of a bone, the stem implant including a stem portion extending longitudinally along a stem axis and a neck portion that extends from the stem portion at an oblique angle relative to the stem axis, the surgical system comprising:

a manipulator including a robotic arm formed of a plurality of links and joints, wherein the robotic arm supports an end effector comprising a stem insertion tool configured to detachably receive the neck portion of the stem implant;

a navigation system comprising a localizer configured to track a pose of the bone and a pose of the end effector; and one or more controllers coupled to the manipulator and the navigation system, the one or more controllers being configured to:

obtain a surgical plan defining a final implant position of the stem implant relative to the cavity of the bone;

acquire, from the navigation system, the tracked poses of the bone and the end effector; and based on the tracked poses and the surgical plan, control the manipulator to enable movement of the end effector while the neck portion of the stem implant is received by the stem insertion tool to enable insertion of the stem implant into the cavity in a first orientation until the stem implant has moved into the cavity to a first insertion depth, and thereafter enable further insertion of the stem implant into the cavity according to a second orientation that differs from the first orientation until the stem implant is advanced to the final implant position.

2. The surgical system of claim 1, wherein:

the surgical plan comprises an insertion path for inserting the stem implant into the cavity, the insertion path defining the first orientation, the second orientation, and the first insertion depth; and the one or more controllers are configured to control the manipulator to enable movement of the stem implant along the insertion path to facilitate insertion of the stem implant into the cavity.

3. The surgical system of claim 1, wherein a cavity creation tool is used to penetrate the bone to form the cavity, and wherein the navigation system is configured to:

determine a final position of the cavity creation tool after penetration of the bone to form the cavity; and determine the final implant position based on the final position of the cavity creation tool.

4. The surgical system of claim 1, wherein the one or more controllers control the manipulator to enable movement of the stem implant by being configured to operate in an automated or a semi-automated mode whereby the manipulator is configured to autonomously direct movement of the stem implant to facilitate insertion of the stem implant into the cavity.

5. The surgical system of claim 4, wherein:

the surgical plan comprises an insertion path for inserting the stem implant into the cavity and the final implant position of the stem implant relative to the cavity; and the one or more controllers control the manipulator in the automated or the semi-automated mode to autonomously direct movement of the stem implant along the insertion path and to the final implant position.

6. The surgical system of claim 1, wherein the one or more controllers control the manipulator to enable movement of the stem implant by being configured to operate in a manual mode whereby the manipulator facilitates movement of the stem implant in response to manual manipulation of the end effector by a user to direct insertion of the stem implant into the cavity.

7. The surgical system of claim 6, wherein:

the surgical plan comprises an insertion path for inserting the stem implant into the cavity; and the one or more controllers control the manipulator in the manual mode to facilitate user-directed movement of the stem implant along the insertion path.

8. The surgical system of claim 7, wherein the one or more controllers are configured to:

detect a deviation of the end effector and/or the stem implant from the insertion path; and provide a haptic feedback through the end effector in response to detection of the deviation.

9. The surgical system of claim 7, wherein the one or more controllers are configured to:

associate a virtual constraint boundary with the insertion path; and control the manipulator in the manual mode to prevent user-directed movement of the end effector and/or the stem implant beyond the virtual constraint boundary associated with the insertion path.

10. The surgical system of claim 6, wherein the one or more controllers are configured to:

detect that the stem implant has reached the final implant position; and provide a haptic feedback through the end effector in response to detection of the stem implant having reached the final implant position.

11. The surgical system of claim 6, wherein the one or more controllers are configured to:

associate a virtual constraint boundary with the final implant position; and control the manipulator in the manual mode to prevent user-directed movement of the end effector and/or the stem implant beyond the virtual constraint boundary associated with the final implant position.

12. The surgical system of claim 1, wherein, during insertion of the stem implant into the cavity, the one or more controllers are configured to:

detect movement of the bone based on the tracked pose of the bone; and control the manipulator to account for movement of the bone.

13. The surgical system of claim 1, wherein the one or more controllers are configured to obtain the surgical plan based on intra-operative planning input.

14. The surgical system of claim 1, further being configured to facilitate insertion of the stem implant into the cavity of the bone for total joint replacement surgery.

* * * * *